(12) United States Patent
Kramer et al.

(10) Patent No.: US 10,028,784 B2
(45) Date of Patent: *Jul. 24, 2018

(54) METHODS AND SYSTEMS FOR USE IN CONTROLLING TISSUE ABLATION VOLUME BY TEMPERATURE MONITORING

(71) Applicant: Dfine, Inc., South Jordan, UT (US)

(72) Inventors: Steve Kramer, Mountain View, CA (US); Kirti P. Kamdar, Los Gatos, CA (US); Andrew Kohm, Foster City, CA (US); Robert Poser, Scotts Valley, CA (US); Aaron Germain, Campbell, CA (US)

(73) Assignee: DFINE, INC., South Jordan, UT (US)

( * ) Notice: Subject to any disclaimer, the term of this patent is extended or adjusted under 35 U.S.C. 154(b) by 87 days.

This patent is subject to a terminal disclaimer.

(21) Appl. No.: 14/453,427

(22) Filed: Aug. 6, 2014

(65) Prior Publication Data

US 2014/0350542 A1 Nov. 27, 2014

Related U.S. Application Data

(63) Continuation of application No. 13/793,632, filed on Mar. 11, 2013, now Pat. No. 8,864,760, which is a (Continued)

(51) Int. Cl.
*A61B 18/18* (2006.01)
*A61B 18/14* (2006.01)
(Continued)

(52) U.S. Cl.
CPC .......... *A61B 18/1492* (2013.01); *A61B 18/08* (2013.01); *A61B 18/12* (2013.01);
(Continued)

(58) Field of Classification Search
CPC .......... A61B 2018/00791; A61B 2018/00797; A61B 2018/00815; A61B 2018/008; A61B 2018/21
See application file for complete search history.

(56) References Cited

U.S. PATENT DOCUMENTS 3,140,623 A 7/1964 Hoose
4,411,266 A 10/1983 Cosman
(Continued)

FOREIGN PATENT DOCUMENTS

CN 2841051 11/2006
JP 2004-242936 9/2004
(Continued)

OTHER PUBLICATIONS

European Examination Report dated Dec. 19, 2017 for EP13767383.6.

*Primary Examiner* — Jaymi Della
(74) *Attorney, Agent, or Firm* — Stoel Rives LLP

(57) ABSTRACT

This invention relates to medical methods, instruments and systems for creating a controlled lesion using temperature to control the growth of the lesion. The treatment can be used in any tissue area and is particularly useful in or around a vertebral body. The features relating to the methods and devices described herein can be applied in any region of soft or hard tissue including bone or hard tissue.

11 Claims, 34 Drawing Sheets

Related U.S. Application Data continuation of application No. 13/755,548, filed on Jan. 31, 2013, now Pat. No. 8,591,507, and a continuation of application No. PCT/US2013/024019, filed on Jan. 31, 2013.

(60) Provisional application No. 61/659,604, filed on Jun. 14, 2012, provisional application No. 61/616,359, filed on Mar. 27, 2012.

(51) Int. Cl.
*A61B 18/12* (2006.01)
*A61B 18/08* (2006.01)
A61B 18/20 (2006.01)
A61B 18/00 (2006.01)
A61B 17/16 (2006.01)

(52) U.S. Cl.
CPC ........ *A61B 18/1206* (2013.01); *A61B 18/148* (2013.01); *A61B 18/1477* (2013.01); *A61B 17/1642* (2013.01); *A61B 17/1671* (2013.01); *A61B 18/1815* (2013.01); *A61B 18/20* (2013.01); *A61B 2018/00339* (2013.01); *A61B 2018/00577* (2013.01); *A61B 2018/00642* (2013.01); *A61B 2018/00678* (2013.01); *A61B 2018/00684* (2013.01); *A61B 2018/00702* (2013.01); *A61B 2018/00791* (2013.01); *A61B 2018/00797* (2013.01); *A61B 2018/126* (2013.01); *A61B 2018/1253* (2013.01); *A61B 2218/002* (2013.01); *A61B 2218/007* (2013.01)

(56) References Cited

U.S. PATENT DOCUMENTS

| | | | |
|---|---|---|---|
| 4,456,017 A | 6/1984 | Miles | |
| 4,476,861 A | 10/1984 | Dimakos et al. | |
| 4,595,006 A | 6/1986 | Burke et al. | |
| 5,282,821 A | 2/1994 | Donahue | |
| 5,284,128 A | 2/1994 | Hart | |
| 5,322,505 A | 6/1994 | Krause et al. | |
| 5,449,351 A | 9/1995 | Zohmann | |
| 5,458,597 A * | 10/1995 | Edwards | A61N 5/045 604/21 |
| 5,599,346 A | 2/1997 | Edwards et al. | |
| 5,620,447 A | 4/1997 | Smith et al. | |
| 5,628,771 A * | 5/1997 | Mizukawa | A61B 18/18 606/31 |
| 5,662,680 A | 9/1997 | Desai | |
| 5,695,513 A | 12/1997 | Johnson et al. | |
| 5,697,536 A | 12/1997 | Daniel et al. | |
| 5,810,804 A * | 9/1998 | Gough | A61B 18/1477 604/22 |
| 5,833,632 A | 11/1998 | Jacobsen et al. | |
| 5,849,028 A * | 12/1998 | Chen | A61B 18/1492 606/41 |
| 5,851,212 A | 12/1998 | Zirps et al. | |
| 5,902,251 A * | 5/1999 | vanHooydonk | A61B 18/18 600/549 |
| 5,921,956 A | 7/1999 | Grinberg et al. | |
| 5,928,239 A | 7/1999 | Mirza | |
| 5,944,715 A | 8/1999 | Goble et al. | |
| 6,073,051 A | 6/2000 | Sharkey et al. | |
| 6,106,524 A | 8/2000 | Eggers et al. | |
| 6,123,702 A * | 9/2000 | Swanson | A61B 18/1206 606/34 |
| 6,135,999 A * | 10/2000 | Fanton | A61B 17/1626 606/38 |
| 6,231,615 B1 | 5/2001 | Preissman | |
| 6,280,441 B1 | 8/2001 | Ryan | |
| 6,409,722 B1 * | 6/2002 | Hoey | A61B 18/1206 606/34 |
| 6,440,138 B1 | 8/2002 | Reiley et al. | |
| 6,447,506 B1 | 9/2002 | Swanson et al. | |
| 6,464,683 B1 | 10/2002 | Samuelson et al. | |
| 6,478,793 B1 | 11/2002 | Cosman et al. | |
| 6,602,248 B1 | 8/2003 | Sharps et al. | |
| 6,622,731 B2 | 9/2003 | Daniel et al. | |
| 6,863,672 B2 | 3/2005 | Reiley et al. | |
| 6,881,214 B2 | 4/2005 | Cosman et al. | |
| 7,022,133 B2 | 4/2006 | Yee et al. | |
| 7,108,696 B2 | 9/2006 | Daniel et al. | |
| 7,156,843 B2 | 1/2007 | Skarda | |
| 7,186,234 B2 | 3/2007 | Dahla et al. | |
| 7,267,683 B2 | 9/2007 | Sharkey et al. | |
| 7,270,661 B2 | 9/2007 | Dahla et al. | |
| 7,480,533 B2 | 1/2009 | Cosman et al. | |
| 7,503,920 B2 | 3/2009 | Siegal | |
| 7,569,054 B2 | 8/2009 | Michelson | |
| 7,595,634 B2 | 9/2009 | Flandre et al. | |
| 7,625,364 B2 | 12/2009 | Corcoran et al. | |
| 7,905,884 B2 | 3/2011 | Simonton et al. | |
| 8,246,627 B2 | 8/2012 | Vanleeuwen et al. | |
| 8,591,507 B2 | 11/2013 | Kramer et al. | |
| 8,663,226 B2 | 3/2014 | Germain | |
| 8,758,349 B2 | 6/2014 | Germain et al. | |
| 8,864,760 B2 | 10/2014 | Kramer et al. | |
| 9,113,974 B2 | 8/2015 | Germain | |
| 9,125,671 B2 | 9/2015 | Germain et al. | |
| 9,161,809 B2 | 10/2015 | Germain et al. | |
| 2002/0026197 A1 | 2/2002 | Foley et al. | |
| 2002/0133148 A1 | 9/2002 | Daniel et al. | |
| 2003/0014094 A1 | 1/2003 | Hammack et al. | |
| 2003/0130664 A1 | 7/2003 | Boucher et al. | |
| 2003/0212394 A1 | 11/2003 | Pearson et al. | |
| 2003/0212395 A1 | 11/2003 | Woloszko et al. | |
| 2004/0087936 A1 | 5/2004 | Stern et al. | |
| 2005/0055030 A1 | 3/2005 | Falahee | |
| 2005/0090852 A1 | 4/2005 | Layne et al. | |
| 2005/0177210 A1 * | 8/2005 | Leung | A61B 18/148 607/101 |
| 2005/0216018 A1 | 9/2005 | Sennett | |
| 2006/0025763 A1 * | 2/2006 | Nelson | A61B 18/1492 606/41 |
| 2006/0085009 A1 | 4/2006 | Truckai et al. | |
| 2006/0264819 A1 | 11/2006 | Fischer et al. | |
| 2007/0055281 A1 | 3/2007 | Osorio et al. | |
| 2007/0156130 A1 | 7/2007 | Thistle | |
| 2008/0004615 A1 | 1/2008 | Woloszko et al. | |
| 2008/0033422 A1 * | 2/2008 | Turner | A61B 18/18 606/33 |
| 2008/0058821 A1 | 3/2008 | Maurer et al. | |
| 2008/0183165 A1 | 7/2008 | Buysee et al. | |
| 2008/0208255 A1 | 8/2008 | Siegal | |
| 2008/0228192 A1 | 9/2008 | Beyar et al. | |
| 2008/0249525 A1 | 10/2008 | Lee et al. | |
| 2009/0131948 A1 | 5/2009 | Liu et al. | |
| 2009/0264892 A1 | 10/2009 | Beyar et al. | |
| 2009/0299282 A1 | 12/2009 | Lau et al. | |
| 2010/0082033 A1 | 4/2010 | Germain | |
| 2010/0152724 A1 * | 6/2010 | Marion | A61B 5/01 606/33 |
| 2010/0211076 A1 | 8/2010 | Germain et al. | |
| 2011/0034884 A9 | 2/2011 | Pellegrino et al. | |
| 2011/0295261 A1 | 4/2011 | Germain | |
| 2011/0160737 A1 | 6/2011 | Steffen et al. | |
| 2011/0251615 A1 | 10/2011 | Truckai et al. | |
| 2011/0295262 A1 | 12/2011 | Germain et al. | |
| 2011/0301590 A1 * | 12/2011 | Podhajsky | A61B 18/14 606/34 |
| 2012/0130381 A1 | 5/2012 | Germain | |
| 2012/0330301 A1 | 12/2012 | Pellegrino et al. | |
| 2013/0231654 A1 | 9/2013 | Germain | |
| 2013/0261621 A1 | 10/2013 | Kramer et al. | |
| 2014/0135779 A1 | 5/2014 | Germain | |
| 2014/0163566 A1 | 6/2014 | Phan et al. | |

(56) References Cited

U.S. PATENT DOCUMENTS

2014/0371740 A1 12/2014 Germain et al.
2015/0313614 A1 11/2015 Germain

FOREIGN PATENT DOCUMENTS

| | | |
|---|---|---|
| JP | 2008510530 | 4/2008 |
| JP | 2008528081 | 7/2008 |
| JP | 2008541878 | 11/2008 |
| JP | 2010063887 | 3/2010 |
| JP | 2011500156 | 1/2011 |
| WO | WO 1993/004634 | 3/1993 |
| WO | WO 1997/003611 | 2/1997 |
| WO | WO 2003/101308 | 12/2003 |
| WO | WO 2008/076330 | 6/2008 |
| WO | WO 2008/084479 | 7/2008 |
| WO | WO 2010/039894 | 4/2010 |
| WO | WO 2010/081187 | 7/2010 |
| WO | 2011114602 | 9/2011 |
| WO | WO 2011/137357 | 11/2011 |
| WO | WO 2011/137377 | 11/2011 |
| WO | WO 2012/071464 | 5/2012 |
| WO | WO 2013/147990 | 10/2013 |
| WO | WO 2014/093673 | 6/2014 |

* cited by examiner

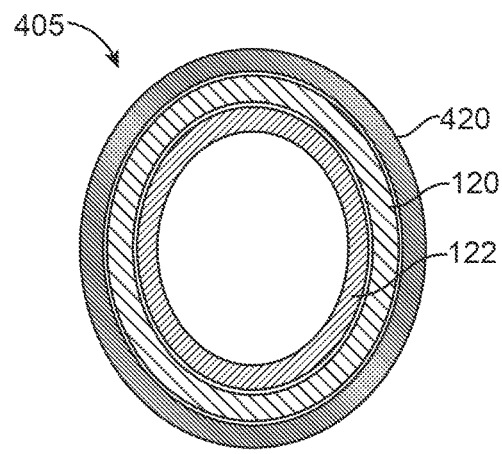
FIG. 12A
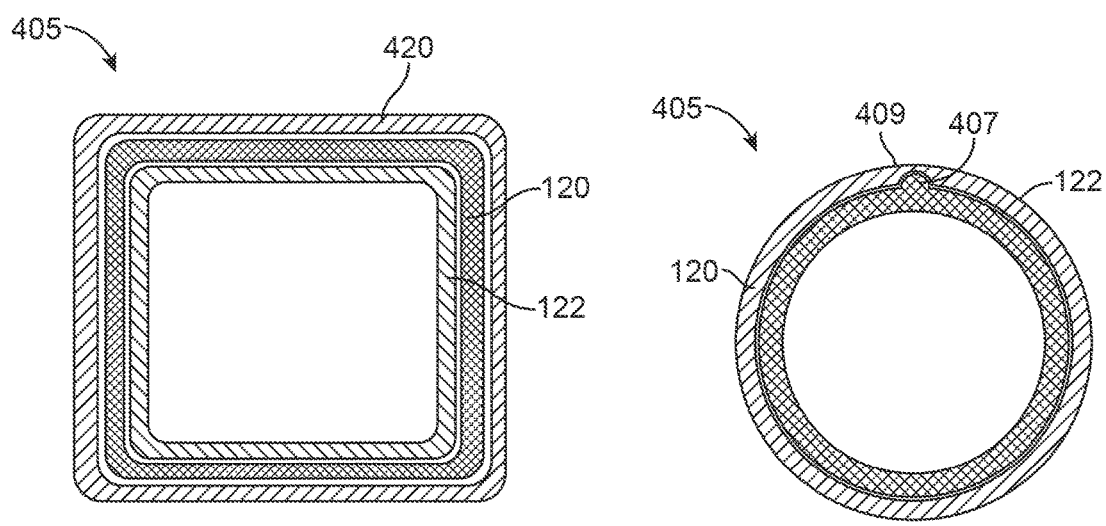
FIG. 12B
FIG. 12C

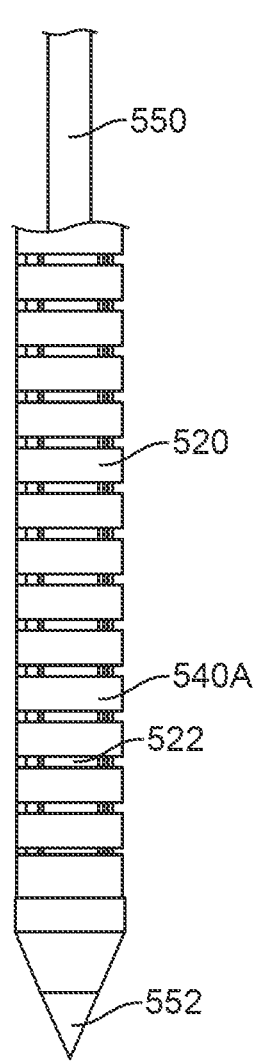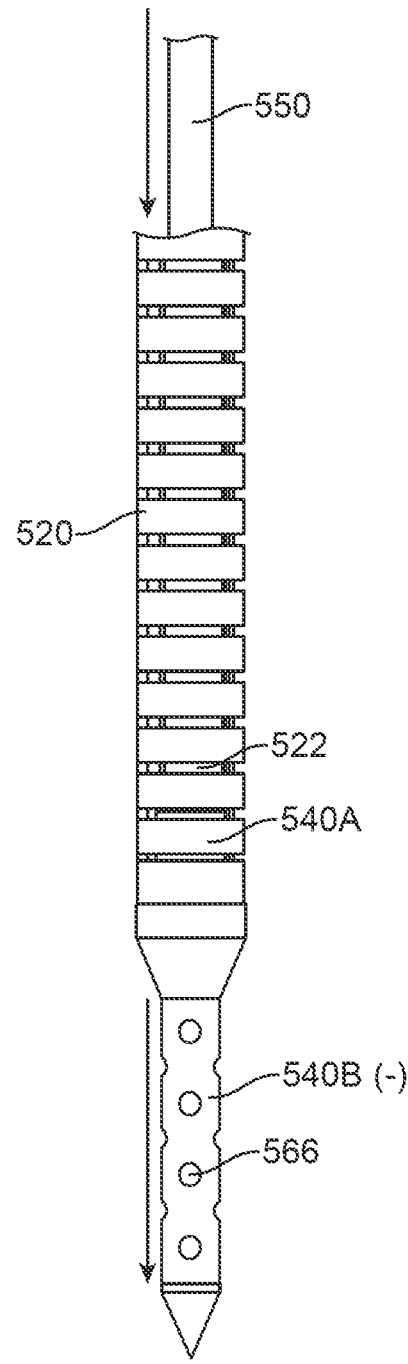
FIG. 18A
FIG. 18B

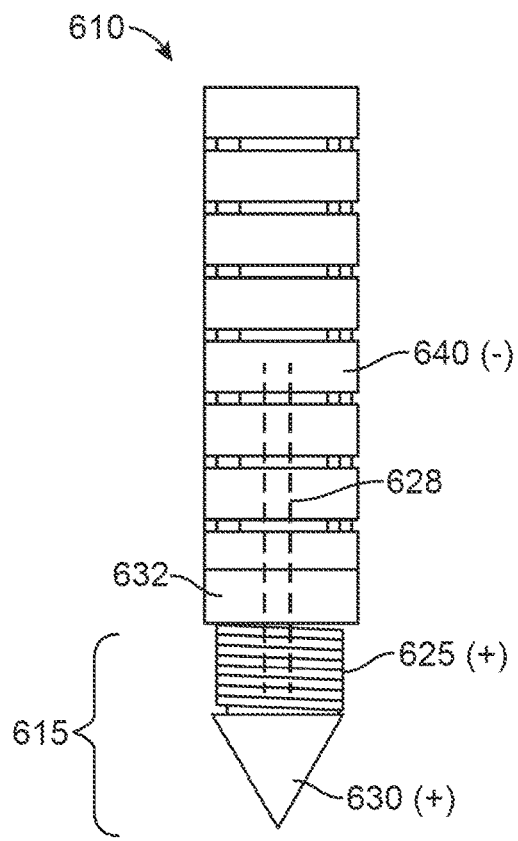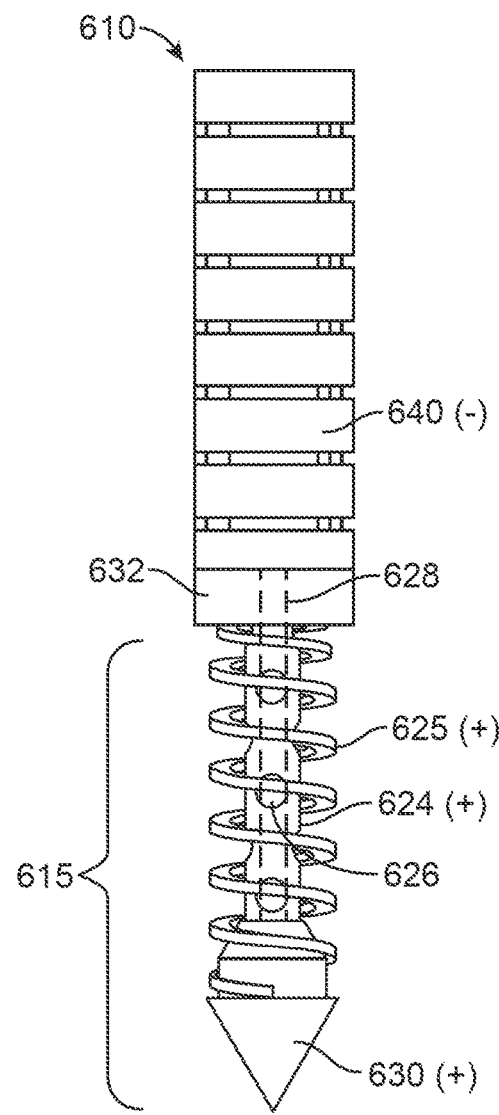
FIG. 22A
FIG. 22B

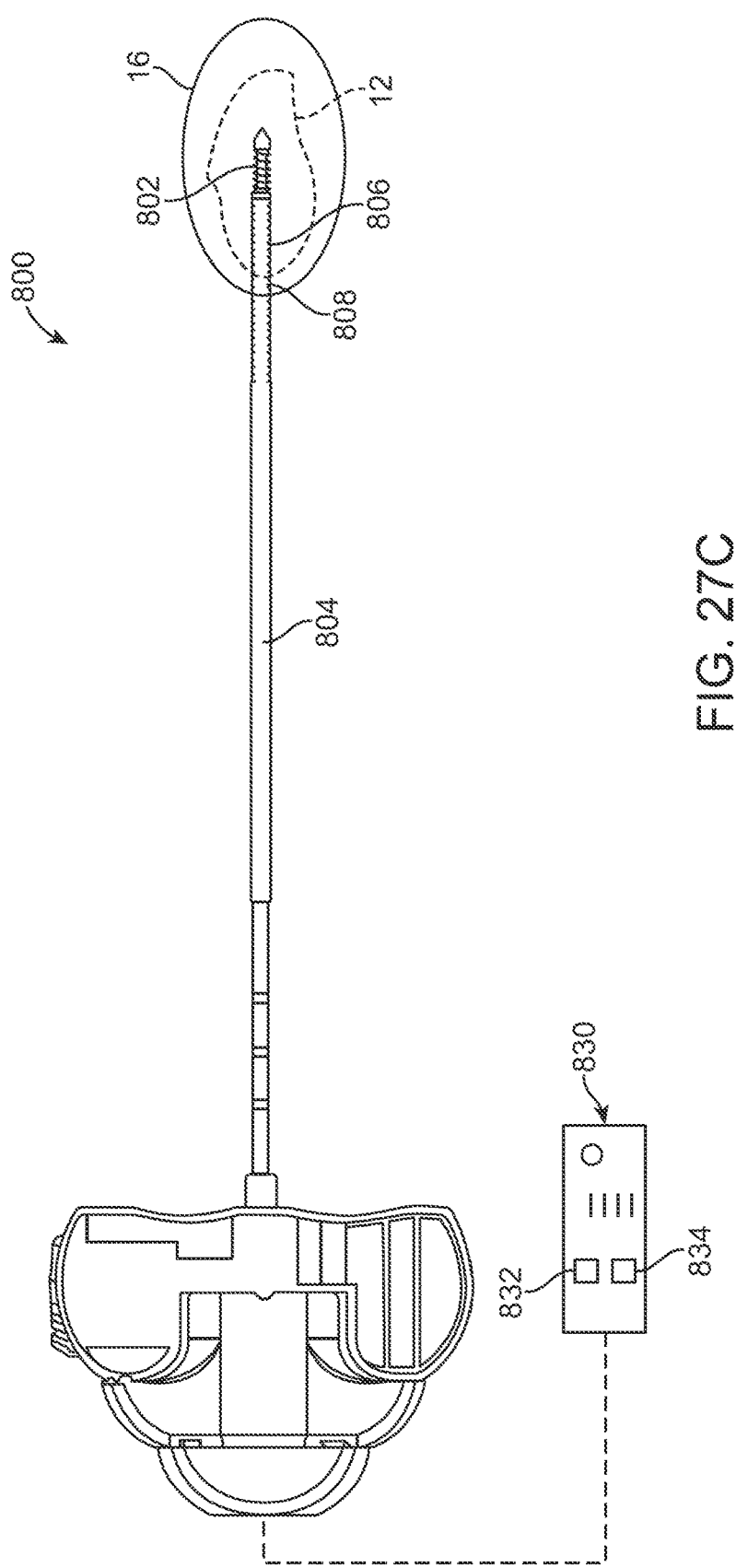

METHODS AND SYSTEMS FOR USE IN CONTROLLING TISSUE ABLATION VOLUME BY TEMPERATURE MONITORING

CROSS-REFERENCE TO RELATED APPLICATIONS

This application is a continuation of U.S. patent application Ser. No. 13/793,632 filed Mar. 11, 2013, which is a continuation of U.S. patent application Ser. No. 13/755,548 filed Jan. 31, 2013, now U.S. Pat. No. 8,591,507, and a continuation of International Patent Application No. PCT/US2013/024019 filed Jan. 31, 2013, both of which are non-provisionals of U.S. Provisional Patent Application No. 61/616,359 filed Mar. 27, 2012 and U.S. Provisional Patent Application No. 61/659,604 filed Jun. 14, 2012, the contents of each of which are incorporated herein by reference in their entirety.

FIELD OF THE INVENTION

This invention relates to medical methods, instruments and systems for creating a controlled lesion using temperature to control the growth of the lesion. The treatment can be used in any tissue area and is particularly useful in or around a vertebral body. The features relating to the methods and devices described herein can be applied in any region of soft or hard tissue including bone or hard tissue.

SUMMARY OF THE INVENTION

Methods and devices described herein relate to improved treatment of tissue using temperature information to assist in producing a desired region of treated tissue and/or using temperature information to produce a region of treated tissue of a known or pre-determined sized.

In one variation, the methods described herein include of applying energy to tissue by positioning a treatment device into a tissue area, the treatment device having an energy transfer portion located at a distal portion of a shaft, the treatment device further including at least a first temperature detecting element coupled to the shaft and axially along the shaft from the energy transfer portion; applying energy to the energy transfer portion to produce a region of heated tissue about the energy transfer portion; continuing application of energy to expand the region of heated tissue; measuring an actual temperature of a tissue area adjacent to the first temperature detecting element; and monitoring a size of the region of heated tissue as it expands by comparing the temperature to at least one associated temperature, such that the associated temperature correlates to a previously measured region of heated tissue having a known size.

The method can include controlling expansion of the region of heated tissue after comparing the temperature to at least one associated temperature. Optionally controlling expansion of the region of heated tissue comprises ceasing application of energy when the temperature reaches the associated temperature.

The areas of tissue that can be treated by the methods and devices described herein include hard and soft tissue. The methods are particularly useful for treatment of a vertebral body and/or a tumor within the vertebral body. However, the method and devices can be applied to any number of body tissues.

In one variation of the methods described herein monitoring the size of the area of heated tissue further comprises determining a characteristic selected from a volume of the region of heated tissue and a length of the region of heated tissue. Monitoring the size of the region of heated tissue can also comprise providing user feedback selected from the group consisting of: the temperature is approaching the associated temperature, the approximated length of the heated tissue.

The methods can also include monitoring the size of the region of heated tissue by adjusting a power supplied to the energy transfer portions during the continuing application of energy to control the growth of the region of heated tissue.

In certain variations, an axial distance between the first temperature detecting element and the energy transfer portion can be adjusted between a plurality of positions, the method further comprising selecting one of the positions to adjust the axial distance between the temperature detecting element and the energy transfer portion.

The associated temperature can comprise a plurality of associated temperatures each corresponding to a plurality of previously measured regions of heated tissue, where each of the plurality of previously measured regions of heated tissue comprises a distinct shape. In such cases the method can further comprise controlling expansion of the region of heated tissue after comparing the temperature to the at least one associated temperature by selecting one of the plurality of associated temperatures and ceasing application of energy when the temperature reaches the selected associated temperature.

In an additional variation, the present disclosure includes a method of using temperature measurements to produce a region of heated tissue in the vertebral body. For example, such a method can comprise inserting a treatment device into a tissue area, the treatment device having an energy transfer portion located at a distal portion of a shaft, the treatment device further including at least one temperature detecting element coupled to the shaft; selecting an actual location in tissue that corresponds to a perimeter of a desired treatment zone having a desired profile; positioning the temperature detecting element at or near the actual location; applying energy to the energy transfer portion to produce the region of heated tissue about the energy transfer portion; continuing application of energy to cause growth of the region of heated tissue; measuring a temperature of a tissue area located adjacent to the temperature detecting element; and comparing the temperature to an associated temperature to control the application of energy to the energy transfer unit, where the associated temperature correlates to a previously determined region of heated tissue having a known profile where the known profile is similar to the desired profile.

Variations of the method can include at least a first temperature detecting element and a second temperature detecting element, where the second temperature detecting element is located proximally to the first temperature detecting element; where measuring the temperature comprises measuring a first temperature and a second temperature at the respective temperature detecting elements; and where comparing the temperature to the associated temperature to control the application of energy to the energy transfer unit comprises selecting either the first or second temperatures to the associated temperature.

The present disclosure also includes medical systems for creating regions of heated tissue using temperature to monitor a desired profile of the regions. For example, the medical system can include: an energy controller capable of controlling energy delivery in response to comparing at least one temperature measurements to at least at least one associated temperature, where the associated temperature correlates to a previously measured region of heated tissue having a known profile; a treatment device having a shaft coupled to a handle, where the handle includes a connector for electrically coupling to the energy control unit; a shaft extending from the handle to a distal portion, an energy transfer portion for delivering energy from the power supply to tissue located at the distal portion; at least a first and second temperature detecting elements spaced proximally from a proximal end of the energy transfer portion, each temperature sensor configured to independently and respectively provide a first and a second actual temperature measurements to the energy controller.

In one variation, the medical system comprises an extendable element and a portion of the shaft, where the extendable element is configured to extend axially relative to a distal end of the shaft. In an additional variation, at least one of the temperature detecting elements is axially moveable along the shaft independently of the energy transfer unit.

The present disclosure also includes medical devices for creating regions of heated tissue using temperature to monitor a desired profile of the regions. Such a medical device can include a shaft coupled to a handle, where the handle includes a connector for electrically coupling to a source of energy; a first temperature detecting element spaced axially proximally along the shaft from a proximal end of the energy transfer portion; a second temperature detecting element spaced proximally from the first temperature detecting element; where the first and second temperature detecting elements are configured to independently and respectively provide a first and a second actual temperature measurements.

The device can further include 34 an energy controller capable of delivering the source of energy to the energy transfer portion, the energy controller configured to control energy delivery in response to comparing at least the first or second actual temperature measurements to at least at least one associated temperature, where the associated temperature correlates to a previously measured region of heated tissue having a known profile.

Another variation of the method includes a method of treating a tumor in or near bone. For example, such a method can include providing an elongated shaft with an articulating working end carrying first and second polarity electrodes; utilizing articulation of the working end to navigate the working end to a position in or near a bone tumor; activating an RF source, such that when activated, current flows between the first and second polarity electrodes to ablate the tumor; and terminating activation of the RF source when a temperature sensor spaced apart from the second polarity electrode reaches a predetermined temperature.

In one variation, the temperature sensor spacing from the second polarity electrode is configured to provide a predetermined tissue ablation volume. In an alternate variation, the shaft has a plurality of temperature sensors spaced apart from the second polarity electrode to provide a plurality of predetermined tissue ablation volumes.

Variations of the device can include one or more lumens that extend through the shaft and working end. These lumens can exit at a distal tip of the device or through a side opening in a wall of the device. The lumen can include a surface comprising a lubricious polymeric material. For example, the material can comprise any bio-compatible material having low frictional properties (e.g., TEFLON®, a polytetrafluroethylene (PTFE), FEP (Fluorinated ethylenepropylene), polyethylene, polyamide, ECTFE (Ethylenechlorotrifluoroethylene), ETFE, PVDF, polyvinyl chloride and silicone).

Variations of the access device and procedures described above include combinations of features of the various embodiments or combination of the embodiments themselves wherever possible.

The methods, devices and systems described herein can be combined with the following commonly assigned patent applications and provisional applications, the entirety of each of which is incorporated by reference herein: application Ser. No. 12/571,174 filed Sep. 30, 2009; application Ser. No. 12/578,455 filed Oct. 13, 2009; application Ser. No. 13/083,411 filed Apr. 8, 2011; application Ser. No. 13/097,998 filed Apr. 29, 2011; application Ser. No. 13/098,116 filed Apr. 29, 2011; application Ser. No. 13/302,927 filed Nov. 22, 2011; Provisional Application No. 61/194,766 filed Sep. 30, 2008; Provisional Application No. 61/104,380 filed Oct. 10, 2008; Provisional Application No. 61/322,281 filed Apr. 8, 2010; Provisional Application No. 61/329,220 filed Apr. 29, 2010; Provisional Application No. 61/329,394 filed Apr. 29, 2010; Provisional Application No. 61/416,042 filed Nov. 22, 2010; Provisional Application No. 61/616,359 filed Mar. 27, 2012; and Provisional Application No. 61/659,604.

BRIEF DESCRIPTION OF DRAWINGS

FIG. 12A is sectional view of another embodiment of working end, taken along line 12A-12A of FIG. 11.
FIGS. 12B and 12C illustrate additional variations of preventing rotation between adjacent sleeves.
FIGS. 18A and 18B illustrate a device having a sharp tip as disclosed herein where the sharp tip is advanceable from the distal end of the shaft.

FIGS. 22A and 22B illustrate the device of FIG. 21 with the helical electrode in a non-extended position and an extended position.

FIGS. 27A to 27C illustrates the use of one or more temperature sensing elements to monitor and/or control the growth of a region of treated tissue.

DETAILED DESCRIPTION

Figures 1, 2:
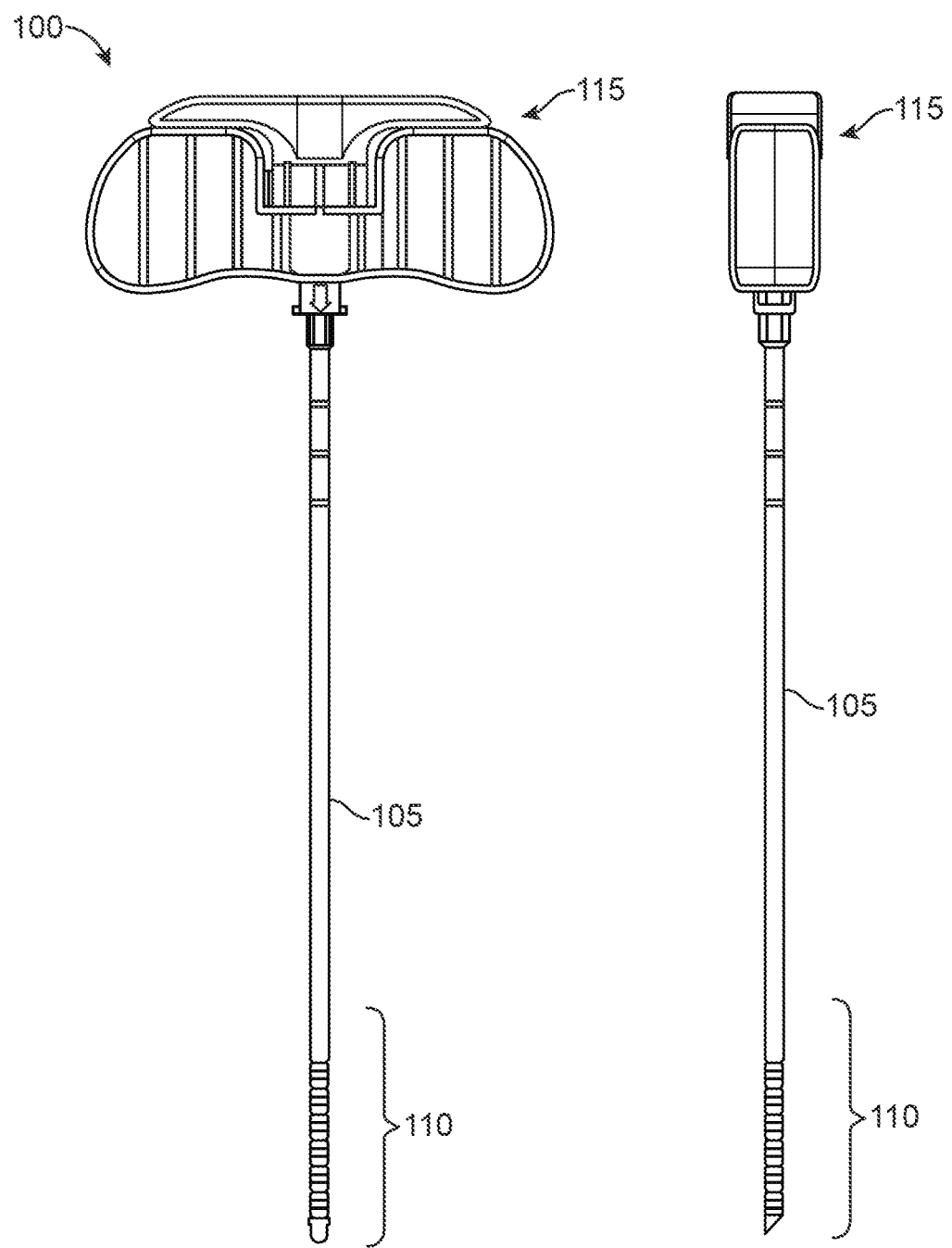
FIG. 1 is a plan view of an osteotome of the invention.
FIG. 2 is a side view of the osteotome of FIG. 1.

Referring to FIGS. 1-5, an apparatus or osteotome 100 is shown that is configured for accessing the interior of a vertebral body and for creating a pathway in vertebral cancellous bone to receive bone cement. In one embodiment, the apparatus is configured with an extension portion or member 105 for introducing through a pedicle and wherein a working end 110 of the extension member can be progressively actuated to curve a selected degree and/or rotated to create a curved pathway and cavity in the direction of the midline of the vertebral body. The apparatus can be withdrawn and bone fill material can be introduced through a bone cement injection cannula. Alternatively, the apparatus 100 itself can be used as a cement injector with the subsequent injection of cement through a lumen 112 of the apparatus.

In one embodiment, the apparatus 100 comprises a handle 115 that is coupled to a proximal end of the extension member 105. The extension member 105 comprises an assembly of first (outer) sleeve 120 and a second (inner) sleeve 122, with the first sleeve 120 having a proximal end 124 and distal end 126. The second sleeve 122 has a proximal end 134 and distal end 136. The extension member 105 is coupled to the handle 115, as will be described below, to allow a physician to drive the extension member 105 into bone while contemporaneously actuating the working end 110 into an actuated or curved configuration (see FIG. 6). The handle 115 can be fabricated of a polymer, metal or any other material suitable to withstand hammering or impact forces used to drive the assembly into bone (e.g., via use of a hammer or similar device on the handle 115). The inner and outer sleeves are fabricated of a suitable metal alloy, such as stainless steel or NiTi. The wall thicknesses of the inner and outer sleeves can range from about 0.005" to 0.010" with the outer diameter the outer sleeve ranging from about 2.5 mm to 5.0 mm.

Figure 3:
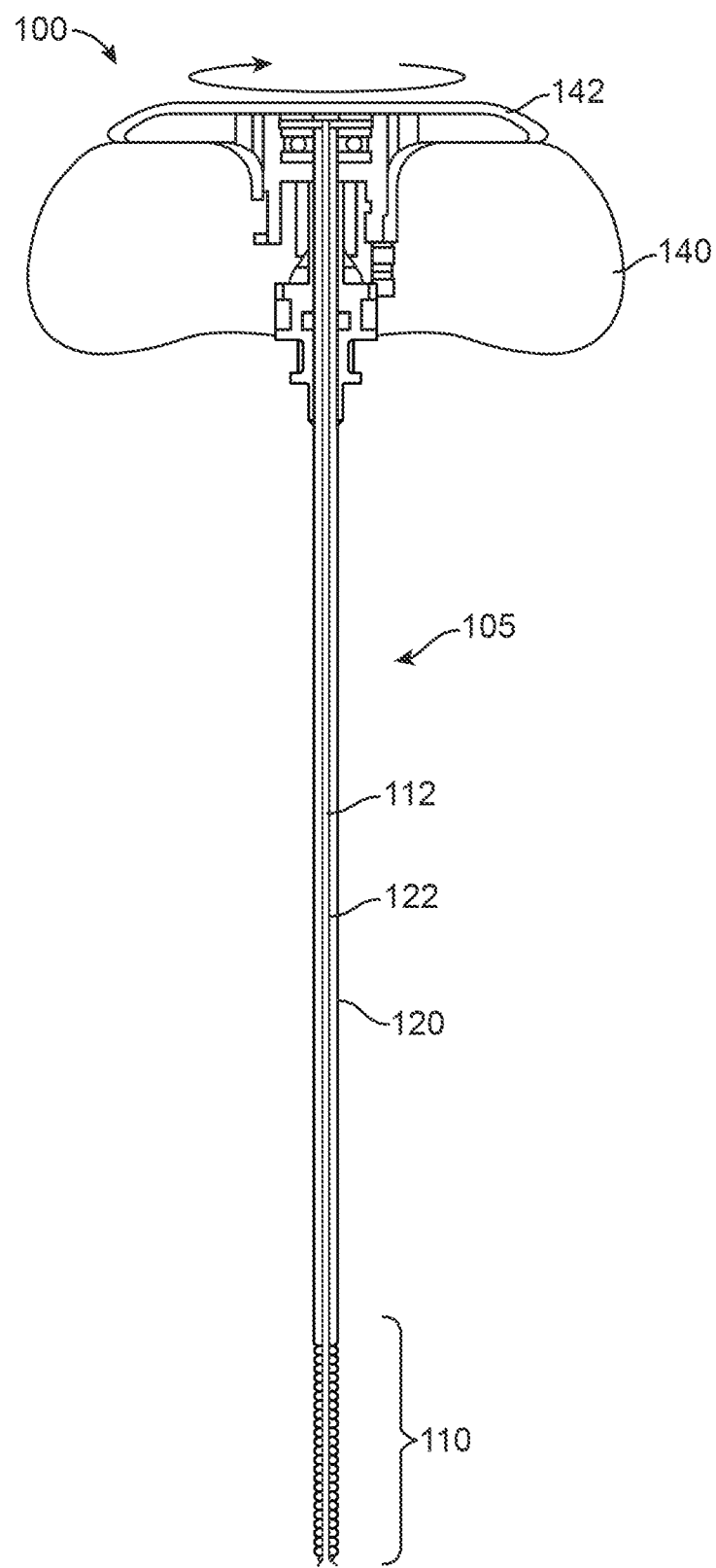
FIG. 3 is a cross sectional view of the osteotome of FIG. 1.
Figure 4:
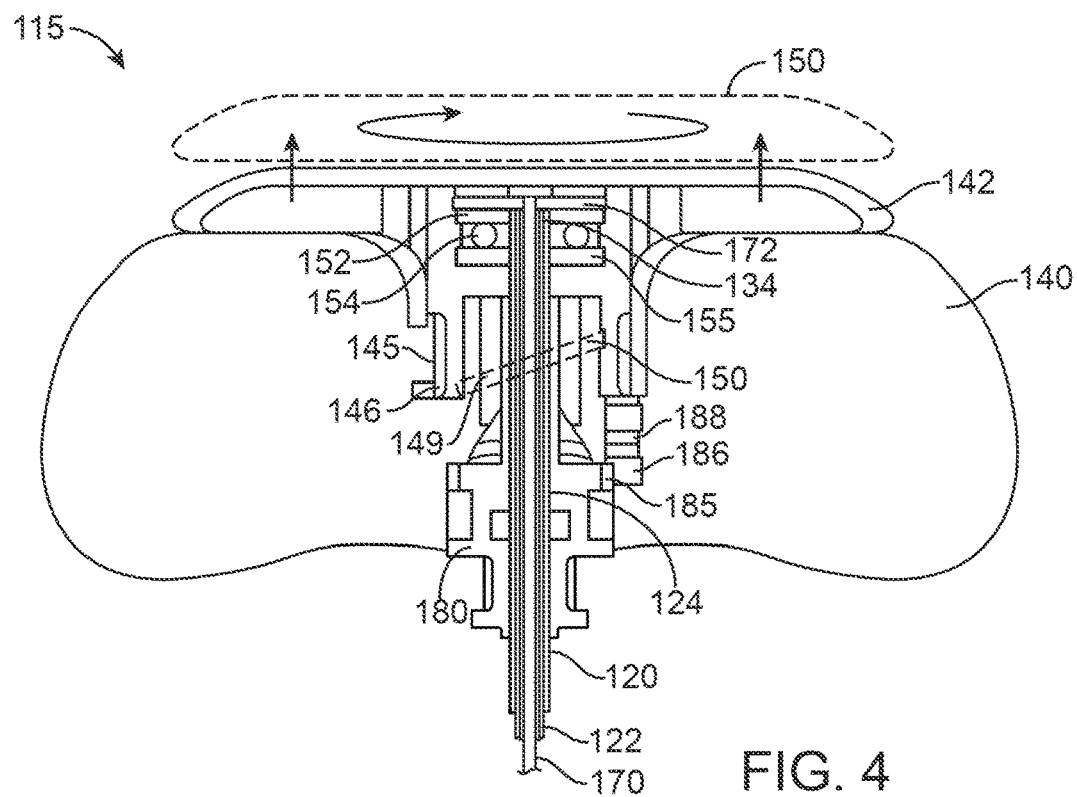
FIG. 4 is an enlarged sectional view of the handle of the osteotome of FIG. 1.

Referring to FIGS. 1, 3 and 4, the handle 115 comprises both a first grip portion 140 and a second actuator portion indicated at 142. The grip portion 140 is coupled to the first sleeve 120 as will be described below. The actuator portion 142 is operatively coupled to the second sleeve 122 as will be described below. The actuator portion 142 is rotatable relative to the grip portion 140 and one or more plastic flex tabs 145 of the grip portion 140 are configured to engage notches 146 in the rotatable actuator portion 142 to provide tactile indication and temporary locking of the handle portions 140 and 142 in a certain degree of rotation. The flex tabs 145 thus engage and disengage with the notches 146 to permit ratcheting (rotation and locking) of the handle portions and the respective sleeve coupled thereto.

The notches or slots in any of the sleeves can comprise a uniform width along the length of the working end or can comprise a varying width. Alternatively, the width can be selected in certain areas to effectuate a particular curved profile. In other variation, the width can increase or decrease along the working end to create a curve having a varying radius. Clearly, it is understood that any number of variations are within the scope of this disclosure.

FIG. 4 is a sectional view of the handle showing a mechanism for actuating the second inner sleeve 122 relative to the first outer sleeve 120. The actuator portion 142 of the handle 115 is configured with a fast-lead helical groove indicated at 150 that cooperates with a protruding thread 149 of the grip portion 140 of the handle. Thus, it can be understood that rotation of the actuation portion 142 will move this portion to the position indicated at 150 (phantom view). In one embodiment, when the actuator portion 142 is rotated a selected amount from about 45° to 720°, or from about 90° to 360°, the inner sleeve 122 is lifted proximally relative to the grip portion 140 and outer sleeve 120 to actuate the working end 110. As can be seen in FIG. 4 the actuator portion 142 engages flange 152 that is welded to the proximal end 132 of inner sleeve 122. The flange 152 is lifted by means of a ball bearing assembly 154 disposed between the flange 152 and metal bearing surface 155 inserted into the grip portion 140 of the handle. Thus, the rotation of actuator 142 can lift the inner sleeve 122 without creating torque on the inner sleeve.

Figure 5:
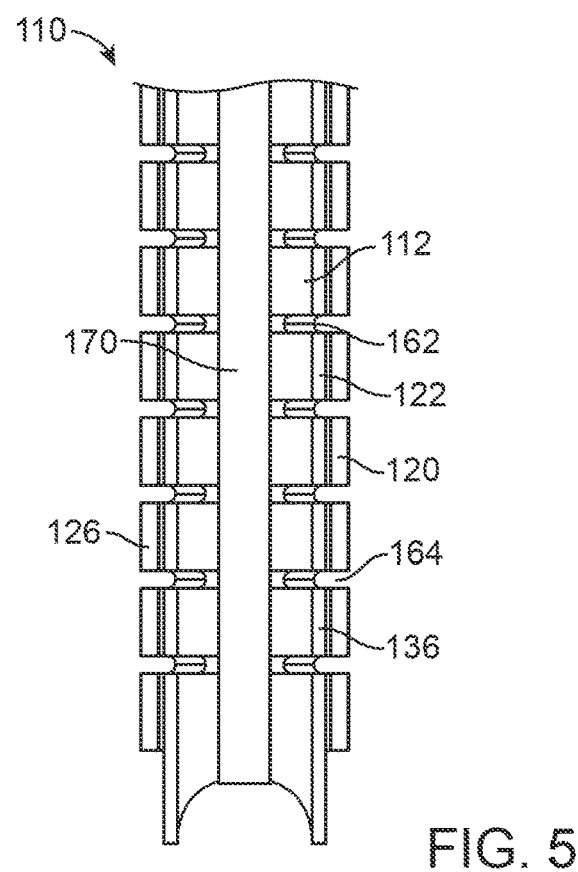
FIG. 5 is an enlarged sectional view of the working end of the osteotome of FIG. 1.
Figure 6A:
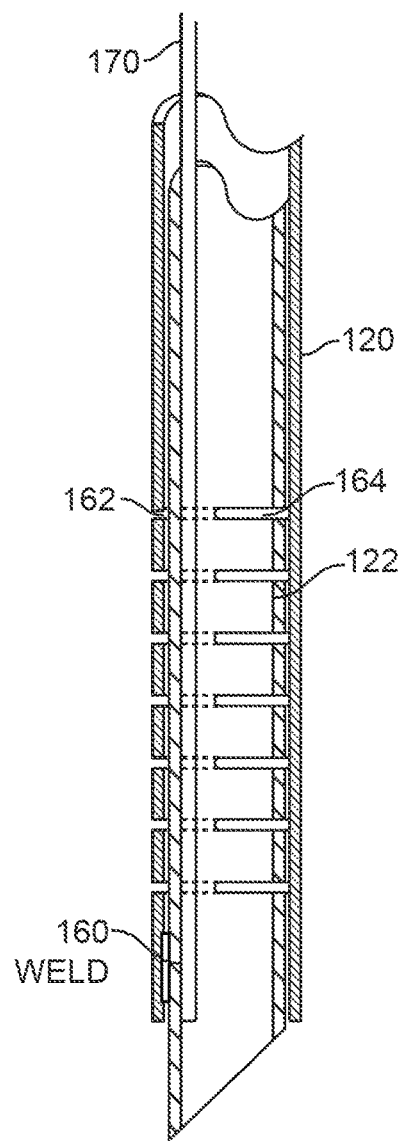
FIG. 6A is a sectional view of the working end of FIG. 5 in a linear configuration.
Figure 6B:
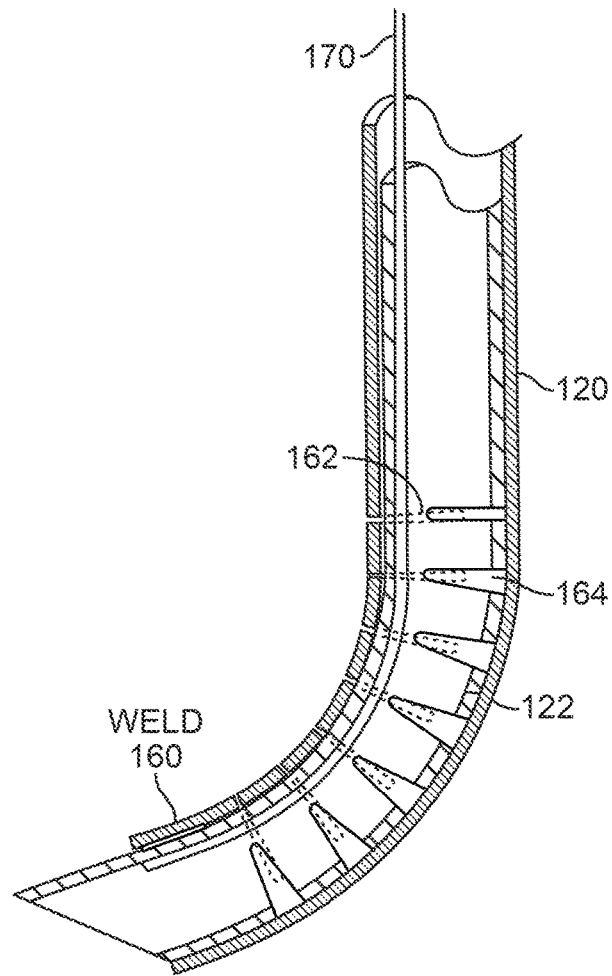
FIG. 6B is a sectional view of the working end of FIG. 5 in a curved configuration.

Now turning to FIGS. 5, 6A and 6B, it can be seen that the working end 110 of the extension member 105 is articulated by cooperating slotted portions of the distal portions of outer sleeve 120 and inner sleeve 122 that are both thus capable of bending in a substantially tight radius. The outer sleeve 120 has a plurality of slots or notches 162 therein that can be any slots that are perpendicular or angled relative to the axis of the sleeve. The inner sleeve 122 has a plurality of slots or notches indicated at 164 that can be on an opposite side of the assembly relative to the slots 162 in the outer sleeve 120. The outer and inner sleeves are welded together at the distal region indicated at weld 160. It thus can be understood that when inner sleeve 122 is translated in the proximal direction, the outer sleeve will be flexed as depicted in FIG. 6B. It can be understood that by rotating the actuator handle portion 142 a selected amount, the working end can be articulated to a selected degree.

FIGS. 4, 5, 6A and 6B further illustrate another element of the apparatus that comprises a flexible flat wire member 170 with a proximal end 171 and flange 172 that is engages the proximal side of flange 152 of the inner sleeve 122. At least the distal portion of the flat wire member 170 is welded to the inner sleeve at weld 175. This flat wire member thus provides a safety feature to retain the working end in the event that the inner sleeve fails at one of the slots 164.

Another safety feature of the apparatus comprises a torque limiter and release system that allows the entire handle assembly 115 to freely rotate—for example if the working end 110 is articulated, as in FIG. 6B, when the physician rotates the handle and when the working end is engaged in strong cancellous bone. Referring to FIG. 4, the grip portion 142 of the handle 115 engages a collar 180 that is fixed to a proximal end 124 of the outer sleeve 120. The collar 180 further comprises notches 185 that are radially spaced about the collar and are engaged by a ball member 186 that is pushed by a spring 188 into notches 185. At a selected force, for example a torque ranging from greater than about 0.5 inch*lbs but less that about 7.5 inch*lbs, 5.0 inch*lbs or 2.5 inch*lbs, the rotation of the handle 115 overcomes the predetermined limit. When the torque limiter assembly is in its locked position, the ball bearing 186 is forced into one of the notches 185 in the collar 180. When too much torque is provided to the handle and outer sleeve, the ball bearing 186 disengages the notch 185 allowing the collar 180 to turn, and then reengages at the next notch, releasing anywhere from 0.5 inch*lbs to 7.5 inch*lbs of torque.

Referring to FIGS. 6A and 6B, it can be understood that the inner sleeve 122 is weakened on one side at its distal portion so as to permit the inner sleeve 122 to bend in either direction but is limited by the location of the notches in the outer sleeve 120. The curvature of any articulated configuration is controlled by the spacing of the notches as well as the distance between each notch peak. The inner sleeve 122 also has a beveled tip for entry through the cortical bone of a vertebral body. Either the inner sleeve or outer sleeve can form the distal tip.

Figure 7A:
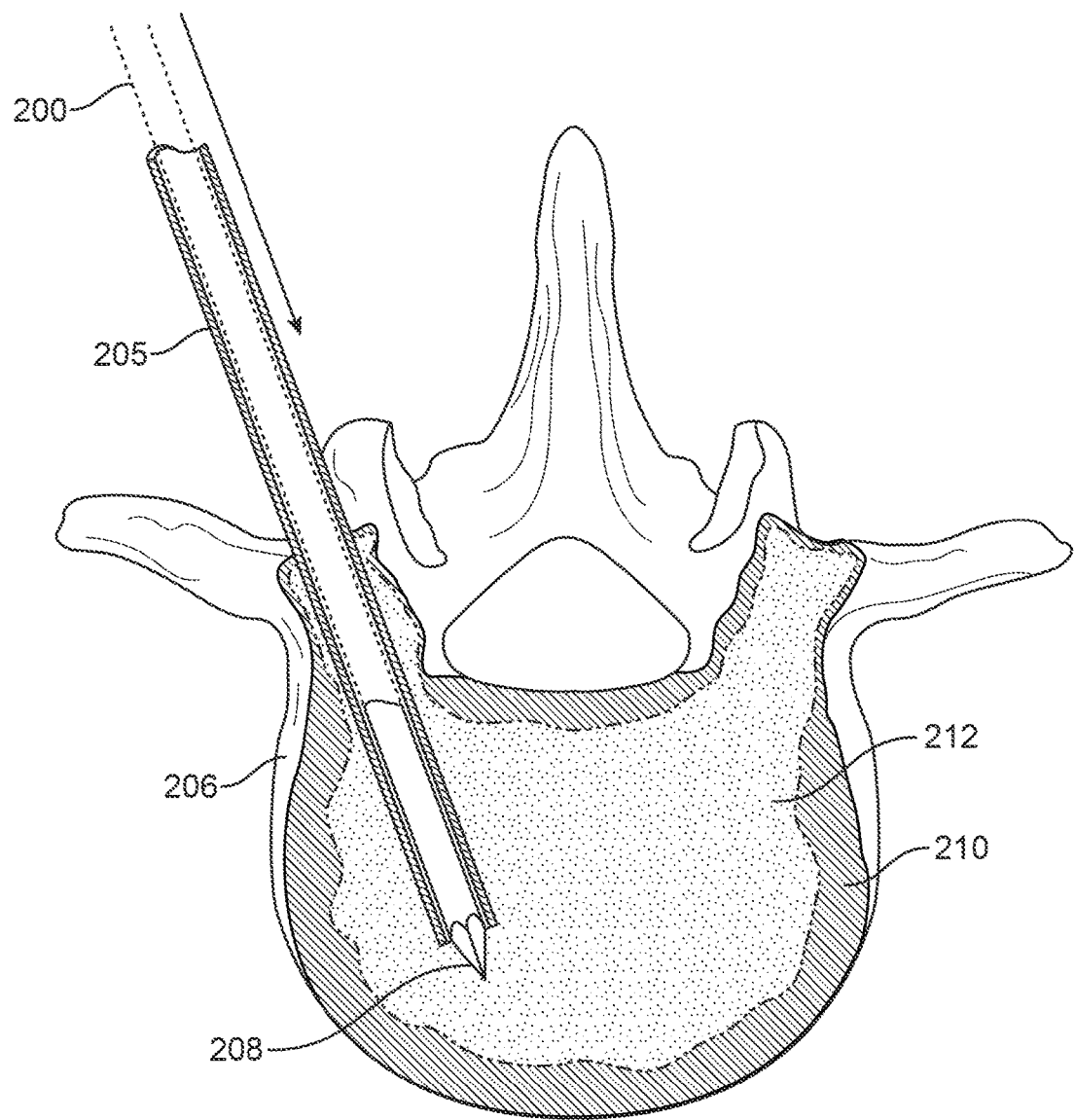
FIGS. 7A-7C are schematic sectional views of a method of use of the osteotome of FIG. 1.
Figure 7B:
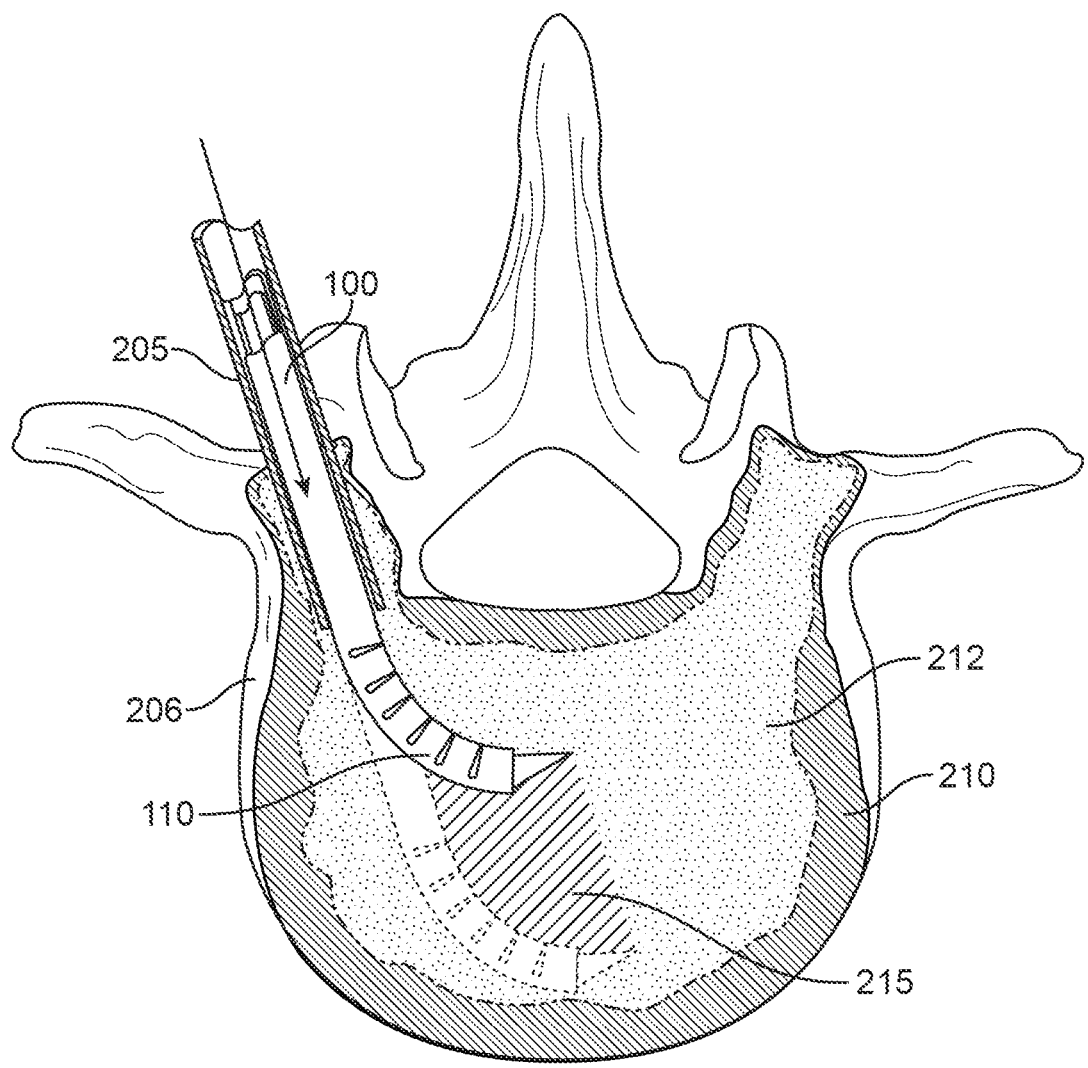
Figure 7C:
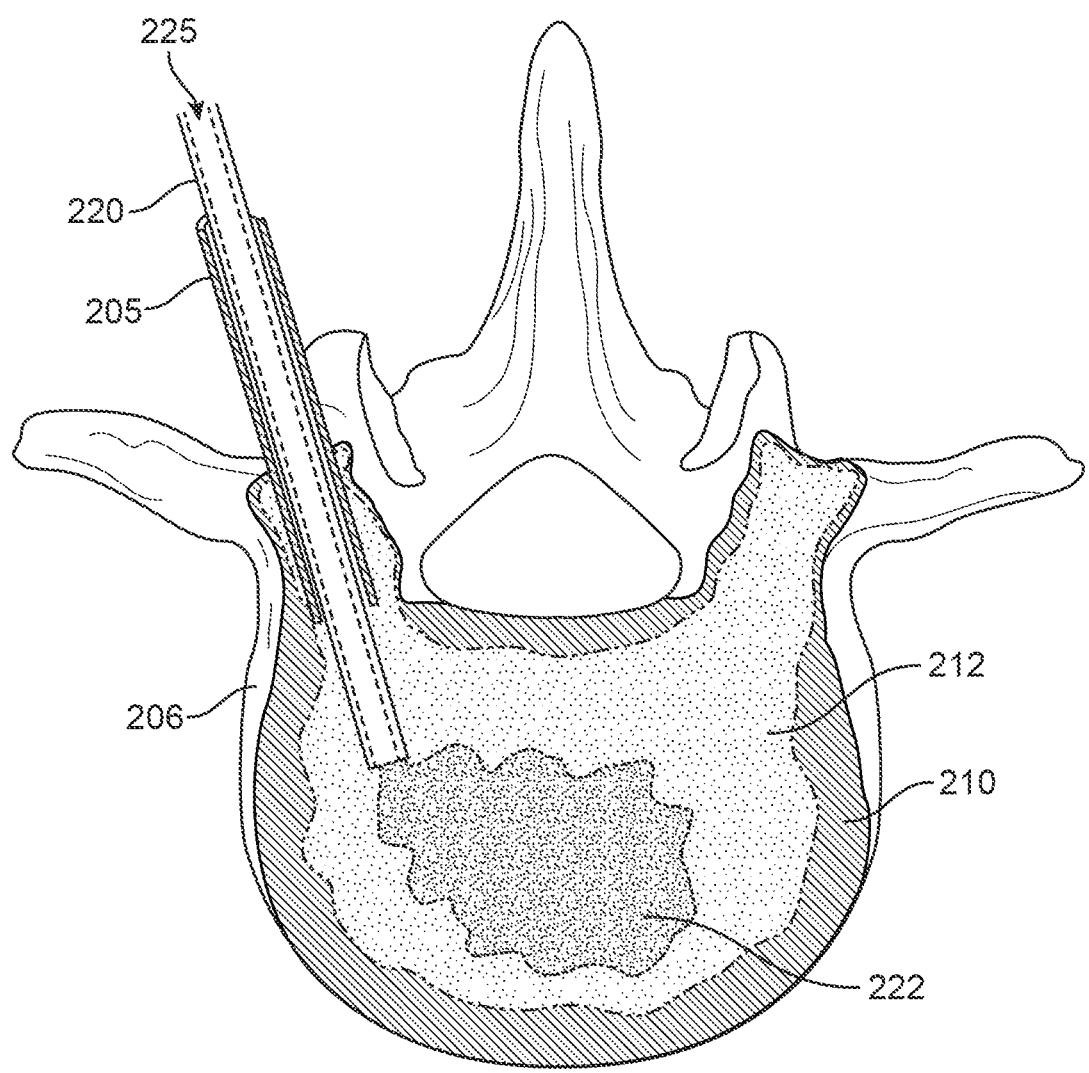

Referring to FIGS. 7A-7C, in one variation of use of the device, a physician taps or otherwise drives a stylet 200 and introducer sleeve 205 into a vertebral body 206 typically until the stylet tip 208 is within the anterior ⅓ of the vertebral body toward cortical bone 210 (FIG. 7A). Thereafter, the stylet 200 is removed and the sleeve 205 is moved proximally (FIG. 7B). As can be seen in FIG. 7B, the tool or osteotome 100 is inserted through the introducer sleeve 205 and articulated in a series of steps as described above. The working end 110 can be articulated intermittently while applying driving forces and optionally rotational forces to the handle 115 to advance the working end through the cancellous bone 212 to create path or cavity 215. The tool is then tapped to further drive the working end 110 to, toward or past the midline of the vertebra. The physician can alternatively articulate the working end 110, and drive and rotate the working end further until imaging shows that the working end 100 has created a cavity 215 of an optimal configuration. Thereafter, as depicted in FIG. 7C, the physician reverses the sequence and progressively straightens the working end 110 as the extension member is withdrawn from the vertebral body 206. Thereafter, the physician can insert a bone cement injector 220 into the path or cavity 215 created by osteotome 100. FIG. 7C illustrates a bone cement 222, for example a PMMA cement, being injected from a bone cement source 225.

In another embodiment (not shown), the apparatus 100 can have a handle 115 with a Luer fitting for coupling a bone cement syringe and the bone cement can be injected through the lumen 112 of the apparatus. In such an embodiment FIG. 9, the lumen can have a lubricious surface layer or polymeric lining 250 to insure least resistance to bone cement as it flows through the lumen. In one embodiment, the surface or lining 250 can be a fluorinated polymer such as TEFLON® or polytetrafluroethylene (PTFE). Other suitable fluoropolymer resins can be used such as FEP and PFA. Other materials also can be used such as FEP (Fluorinated ethylenepropylene), ECTFE (Ethylenechlorotrifluoro-ethylene), ETFE, Polyethylene, Polyamide, PVDF, Polyvinyl chloride and silicone. The scope of the invention can include providing a polymeric material having a static coefficient of friction of less than 0.5, less than 0.2 or less than 0.1.

Figure 9:
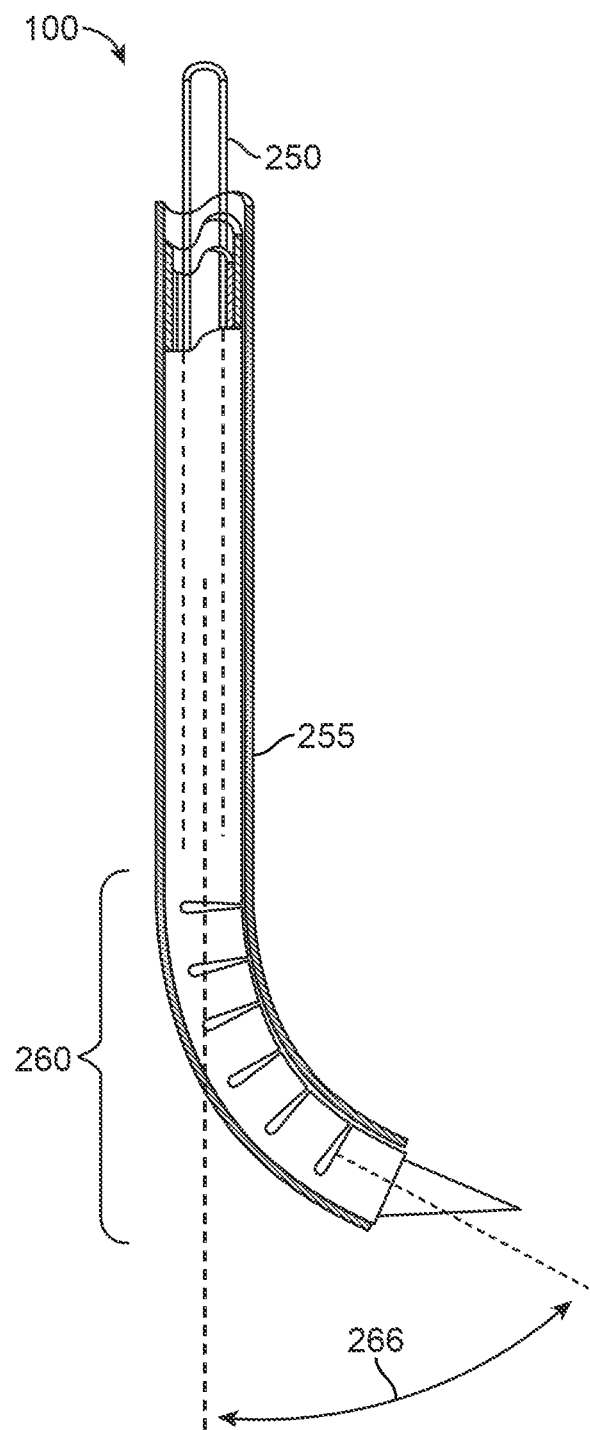
FIG. 9 is another embodiment of an osteotome working end.

FIG. 9 also shows the extension member or shaft 105 can be configured with an exterior flexible sleeve indicated at 255. The flexible sleeve can be any commonly known biocompatible material, for example, the sleeve can comprise any of the materials described in the preceding paragraph.

As also can be seen in FIG. 9, in one variation of the device 100, the working end 110 can be configured to deflect over a length indicated at 260 in a substantially smooth curve. The degree of articulation of the working end 100 can be at least 45°, 90°, 135° or at least 180° as indicated at 265 (FIG. 9). In additional variations, the slots of the outer 120 and inner sleeves 120 can be varied to produce a device having a radius of curvature that varies among the length 260 of the device 100.

In another embodiment of the invention, the inner sleeve can be spring loaded relative the outer sleeve, in such a way as to allow the working end to straighten under a selected level of force when pulled in a linear direction. This feature allows the physician to withdraw the assembly from the vertebral body partly or completely without further rotation the actuating portion 142 of handle 115. In some variations, the force-limiter can be provided to allow less than about 10 inch*lbs of force to be applied to bone.

Figure 8:
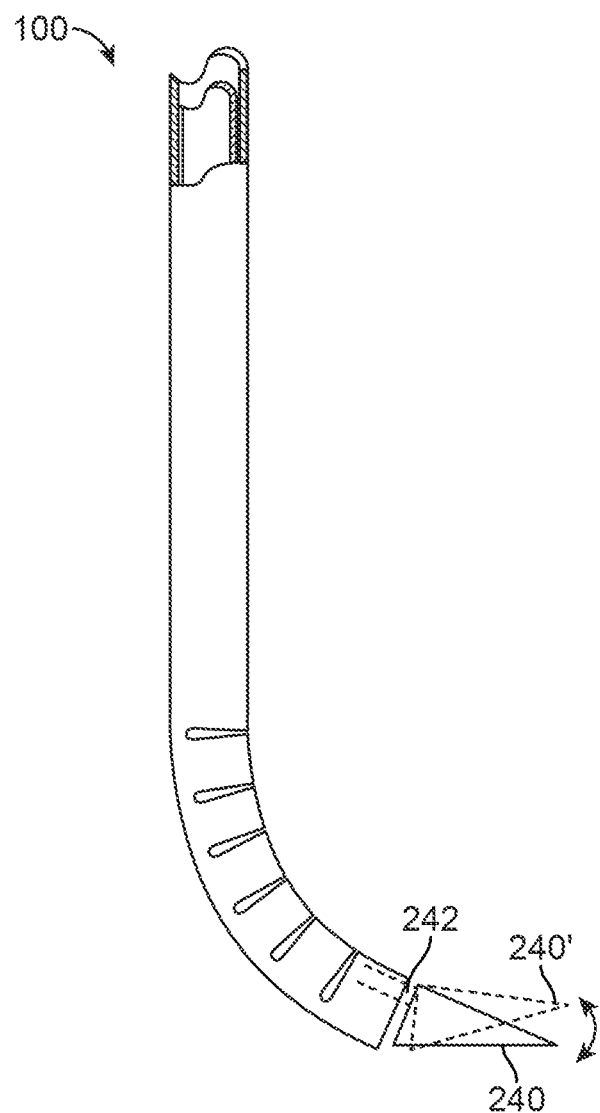
FIG. 8 is another embodiment of an osteotome working end.

In another embodiment shown in FIG. 8, the working end 110 is configured with a tip 240 that deflects to the position indicated at 240' when driven into bone. The tip 240 is coupled to the sleeve assembly by resilient member 242, for example a flexible metal such as stainless steel or NiTi. It has been found that the flexing of the tip 240 causes its distal surface area to engage cancellous bone which can assist in deflecting the working end 110 as it is hammered into bone.

In another embodiment of the invention (not shown), the actuator handle can include a secondary (or optional) mechanism for actuating the working end. The mechanism would include a hammer-able member with a ratchet such that each tap of the hammer would advance assembly and progressively actuate the working end into a curved configuration. A ratchet mechanism as known in the art would maintain the assembly in each of a plurality of articulated configurations. A release would be provided to allow for release of the ratchet to provide for straightening the extension member 105 for withdrawal from the vertebral body.

Figure 10:
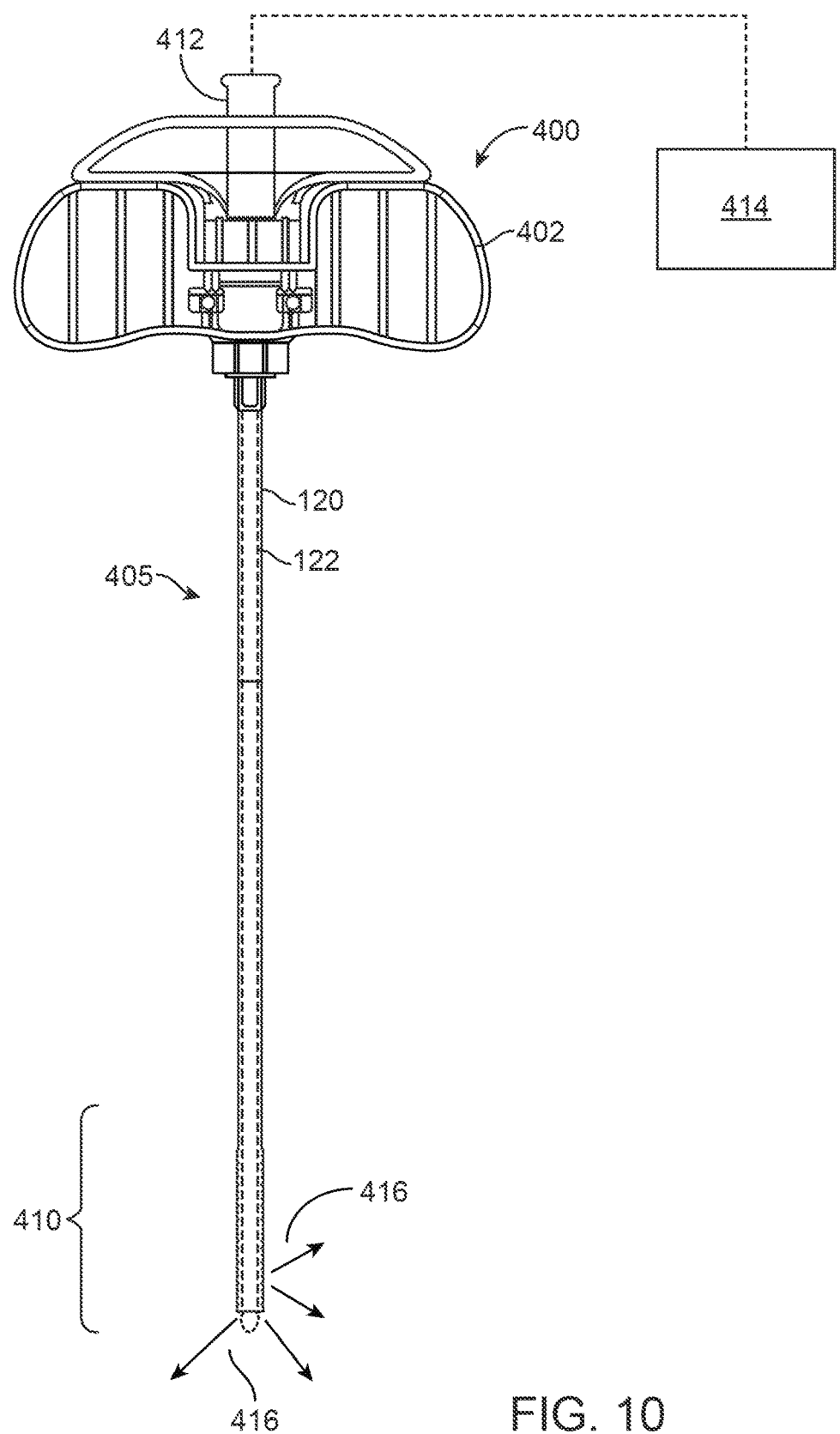
FIG. 10 is another variation of an osteotome with an outer sleeve.
Figure 11:
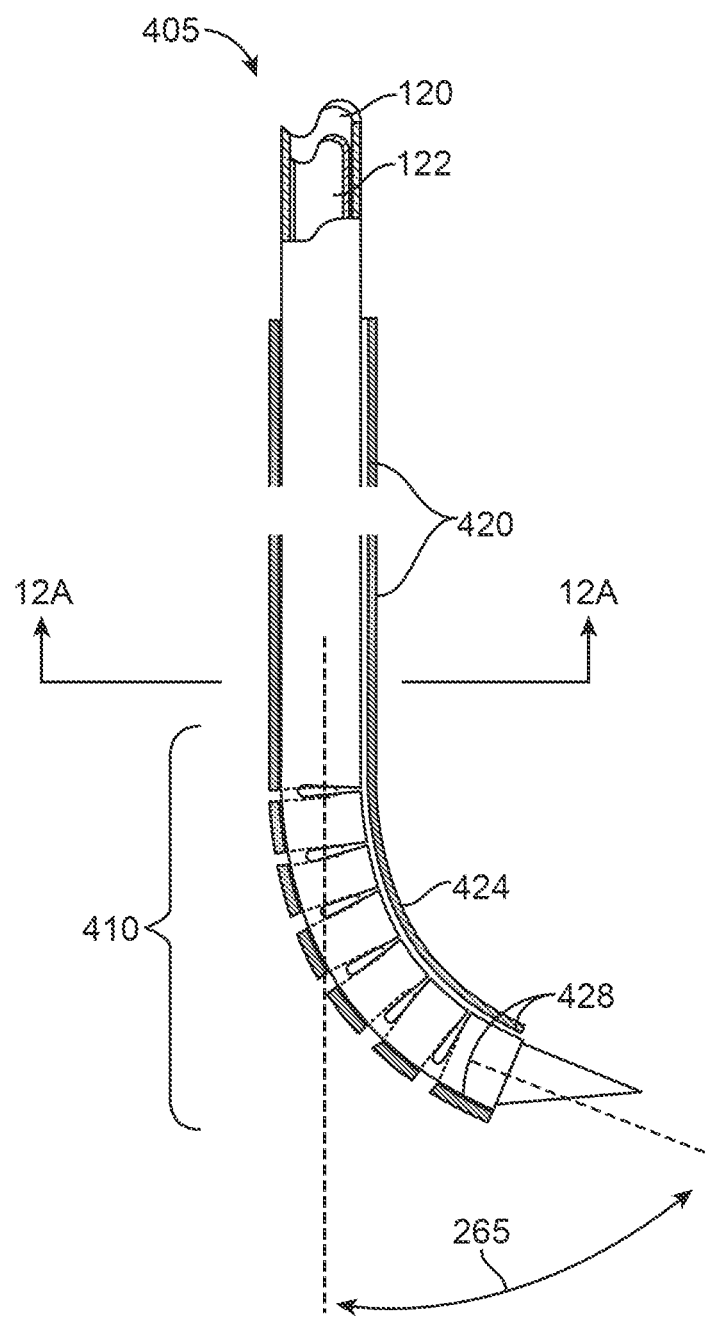
FIG. 11 is a cut-away view of the working end of the osteotome of FIG. 10.

FIGS. 10 and 11 illustrate another variation of a bone treatment device 400 with a handle 402 and extension member 405 extending to working end 410 having a similar construction to that FIGS. 1 to 6B. The device 400 operates as described previously with notched first (outer) sleeve 120 and cooperating notched second (inner) sleeve 122. However, the variation shown in FIGS. 10 and 11 also includes a third concentric notched sleeve 420, exterior to the first 120 and second 122 sleeves. The notches or slots in sleeve 420 at the working end 410 permit deflection of the sleeve as indicated at 265 in FIG. 11.

FIG. 10 also illustrates the treatment device 400 as including a luer fitting 412 that allows the device 402 to be coupled to a source of a filler material (e.g., a bone filler or bone cement material). The luer can be removable from the handle 402 to allow application of an impact force on the handle as described above. Moreover, the luer fitting 402 can be located on the actuating portion of the handle, the stationary part of the handle or even along the sleeve. In any case, variations of the device 400 permit coupling the filler material with a lumen extending through the sleeves (or between adjacent sleeves) to deposit filler material at the working end 410. As shown by arrows 416, filler material can be deposited through a distal end of the sleeves (where the sharp tip is solid) or can be deposited through openings in a side-wall of the sleeves. Clearly, variations of this configuration are within the scope of those familiar in the field.

In some variations, the third notched sleeve 420 is configured with its smooth (non-notched) surface 424 disposed to face inwardly on the articulated working end (FIG. 11) such that a solid surface forms the interior of the curved portion of the working end 410. The smooth surface 424 allows withdrawal of the device 110 into a cannula or introducer 205 without creating a risk that the slots or notches become caught on a cannula 205 (see e.g., FIG. 7B).

As shown in FIGS. 10-11, the third (outermost) sleeve 420 can extend from an intermediate location on the extension member 405 to a distal end of the working end 410. However, variations of the device include the third sleeve 420 extending to the handle 402. However, the third sleeve 420 is typically not coupled to the handle 402 so that any rotational force or torque generated by the handle 402 is not directly transmitted to the third sleeve 420.

In one variation, the third sleeve 420 is coupled to the second sleeve 120 at only one axial location. In the illustrated example shown in FIG. 11, the third sleeve 420 is affixed to second sleeve 420 by welds 428 at the distal end of the working end 410. However, the welds or other attachment means (e.g., a pin, key/keyway, protrusion, etc.) can be located on a medial part of the sleeve 420. The sleeve 420 can be fabricated of any bio-compatible material. For example, in one variation, the third sleeve is fabricated form a 3.00 mm diameter stainless steel material with a wall thickness of 0.007". The first, second and third sleeves are sized to have dimensions to allow a sliding fit between the sleeves.

FIG. 12A is a sectional view of extension member 405 of another variation, similar to that shown in FIGS. 10-11. However, the variation depicted by FIG. 12A comprises non-round configurations of concentric slidable sleeves (double or triple sleeve devices). This configuration limits or prevents rotation between the sleeves and allows the physician to apply greater forces to the bone to create a cavity. While FIG. 12A illustrates an oval configuration, any non-round shape is within the scope of this disclosure. For example, the cross-sectional shape can comprise a square, polygonal, or other radially keyed configuration as shown in FIGS. 12B and 12C. As shown in FIG. 12C the sleeves can include a key 407 and a receiving keyway 409 to prevent rotation but allow relative or axial sliding of the sleeves. The key can comprise any protrusion or member that slides within a receiving keyway. Furthermore, the key can comprise a pin or any raised protrusion on an exterior or interior of a respective sleeve. In this illustration, only the first 122 and second 120 sleeves are illustrated. However, any of the sleeves can be configured with the key/keyway. Preventing rotation between sleeves improves the ability to apply force to bone at the articulated working end.

Figure 13:
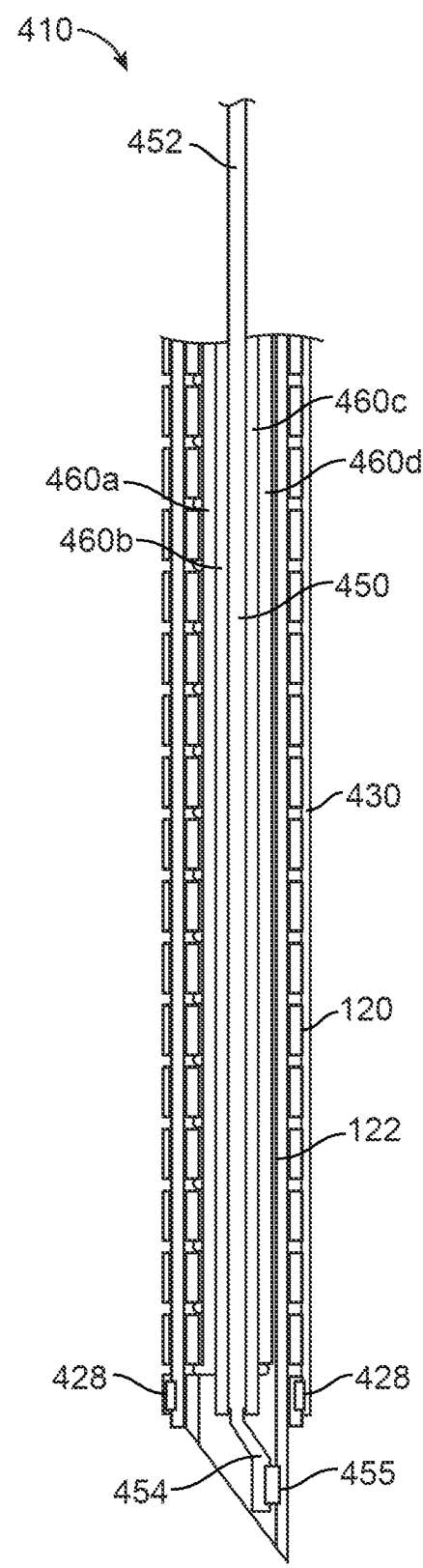
FIG. 13 is sectional view of another working end embodiment similar to that of FIG. 11.
Figure 14:
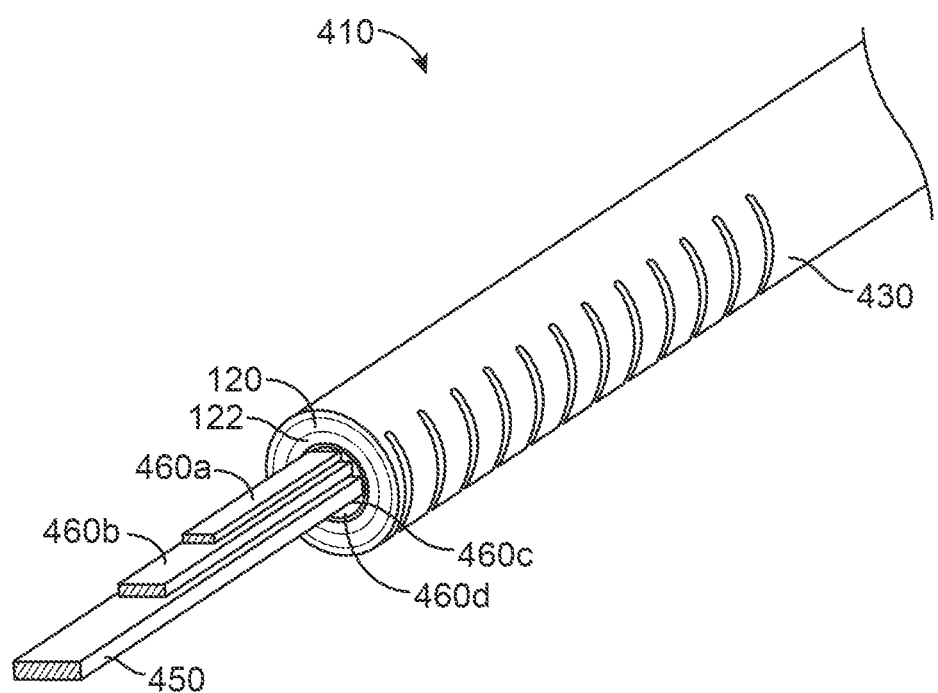
FIG. 14 is a cut-away perspective view of the working end of FIG. 13.

FIGS. 13-14 illustrate another variation of a working end 410 of an osteotome device. In this variation, the working end 410 includes one or more flat spring elements 450, 460a, 460b, 460c, 460d, that prevent relative rotation of the sleeves of the assembly thus allowing greater rotational forces to be applied to cancellous bone from an articulated working end. The spring elements further urge the working end assembly into a linear configuration. To articulate the sleeves, a rotational force is applied to the handle as described above, once this rotational force is removed, the spring elements urge the working end into a linear configuration. As shown in FIG. 13, one or more of the spring elements can extend through the sleeves for affixing to a handle to prevent rotation. Furthermore, the distal end 454 of flat spring element 450 is fixed to sleeve assembly by weld 455. Thus, the spring element is fixed at each end to prevent its rotation. Alternate variations include one or more spring elements being affixed to the inner sleeve assembly at a medial section of the sleeve.

As shown in FIGS. 13-14, variations of the osteotome can include any number of spring elements 460a-460d. These additional spring elements 460a-460d can be welded at either a proximal or distal end thereof to an adjacent element or a sleeve to allow the element to function as a leaf spring.

Figure 15:
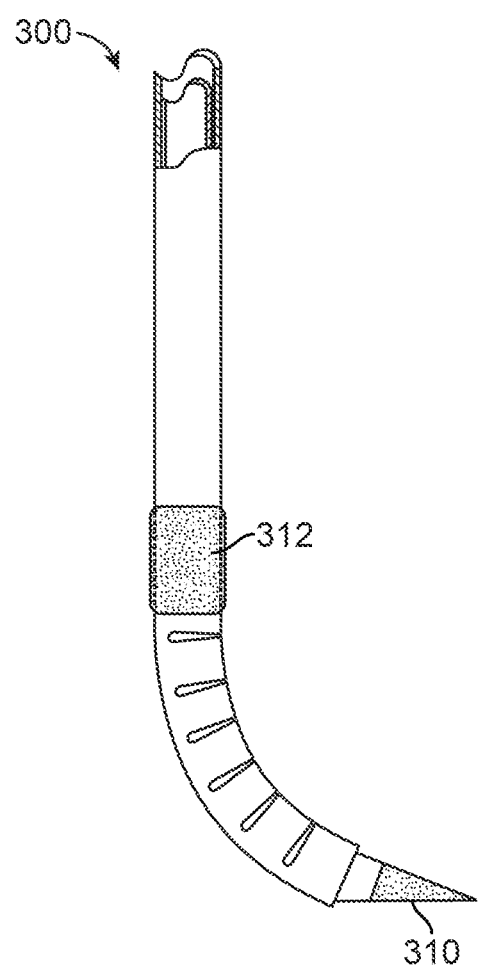
FIG. 15 illustrates a variation of an osteotome as described herein having electrodes on a tip of the device and another electrode on the shaft.

In an additional variation, the osteotome device can include one or more electrodes 310, 312 as shown in FIG. 15. In this particular example, the device 300 includes spaced apart electrodes having opposite polarity to function in a bi-polar manner. However, the device can include a monopolar configuration. Furthermore, one or more electrodes can be coupled to individual channels of a power supply so that the electrodes can be energized as needed. Any variation of the device described above can be configured with one or more electrodes as described herein.

Figure 16:
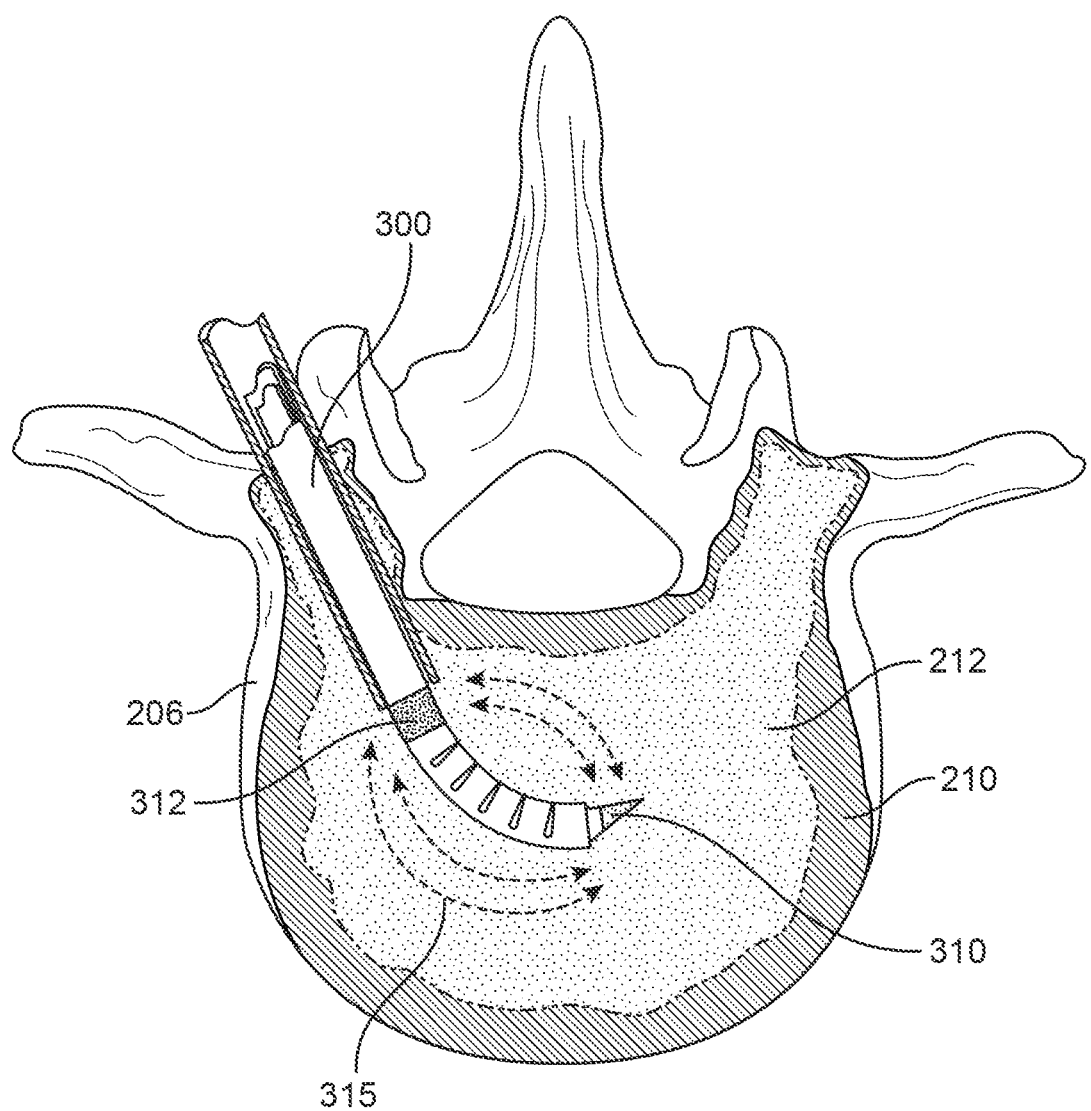
FIG. 16 illustrates an osteotome device as shown in FIG. 15 after being advanced into the body and where current passes between electrodes.

FIG. 16 illustrates an osteotome device 300 after being advanced into the body as discussed above. As shown by lines 315 representing current flow between electrodes, when required, the physician can conduct RF current between electrodes 310 and 312 to apply coagulative or ablative energy within the bone structure of the vertebral body (or other hard tissue). While FIG. 16 illustrates RF current 315 flow between electrodes 310 and 312, variations of the device can include a number of electrodes along the device to apply the proper therapeutic energy. Furthermore, an electrode can be spaced from the end of the osteotome rather than being placed on the sharp tip as shown by electrode 310. In some variations, the power supply is coupled to the inner sharp tip or other working end of the first sleeve. In those variations with only two sleeves, the second pole of the power supply is coupled with the second sleeve (that is the exterior of the device) to form a return electrode. However, in those variations having three sleeves, the power supply can alternatively be coupled with the third outer sleeve. In yet additional variations, the second and third sleeves can both function as return electrodes. However, in those devices that are monopolar, the return electrode will be placed outside of the body on a large area of skin.

FIGS. 17 to 20 illustrate another variation of an articulating probe or osteotome device 500. In this variation, the device 500 includes a working end 505 that carries one or more RF electrodes that can be used to conduct current therethrough. Accordingly, the device can be used to sense impedance of tissue, locate nerves, or simply apply electrosurgical energy to tissue to coagulate or ablate tissue. In one potential use, the device 500 can apply ablative energy to a tumor or other tissue within the vertebra as well as create a cavity.

Figure 17:
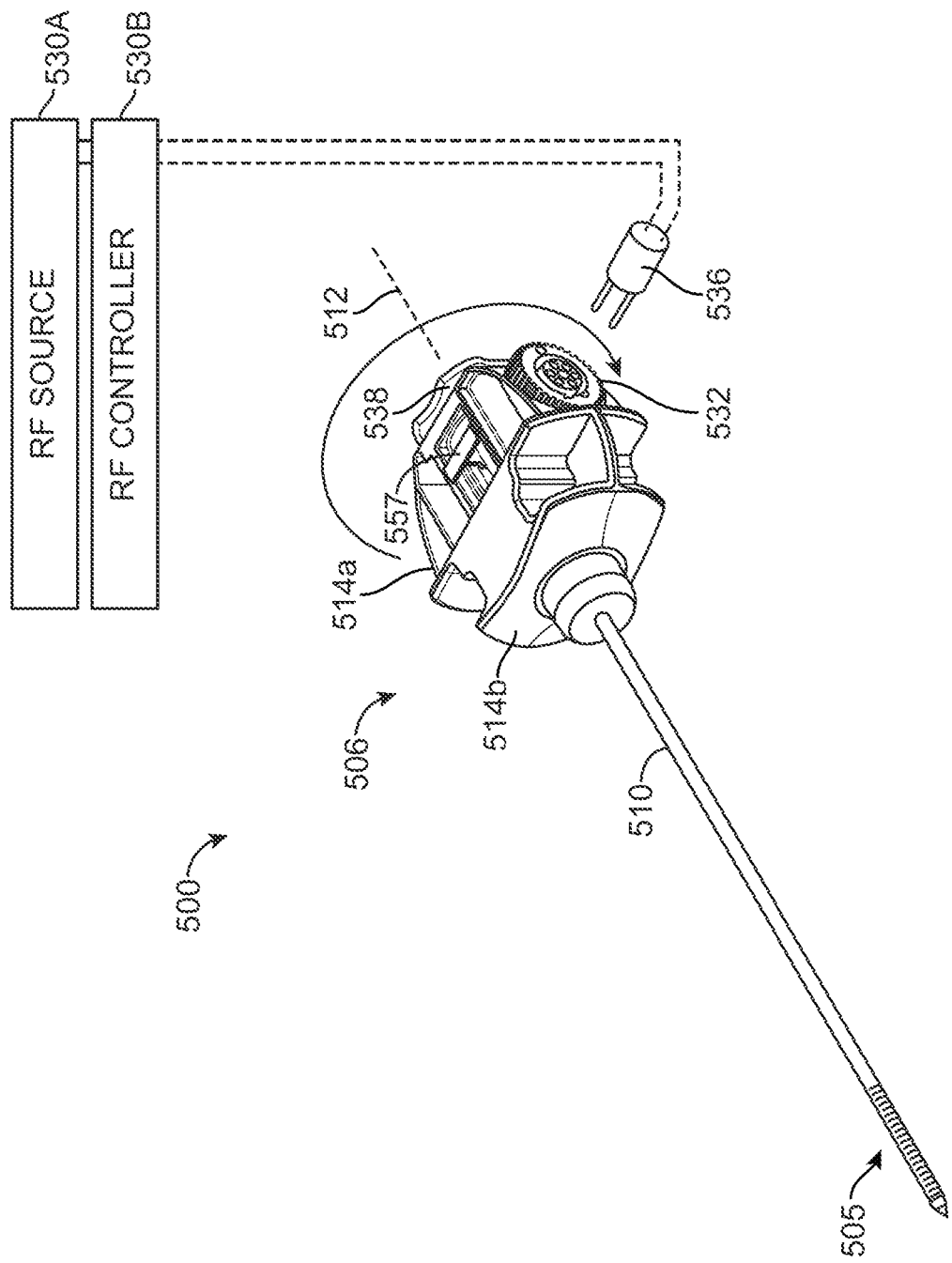
FIG. 17 illustrates a variation of a device as described herein further including a connector for providing energy at the working end of the device.
Figure 19:
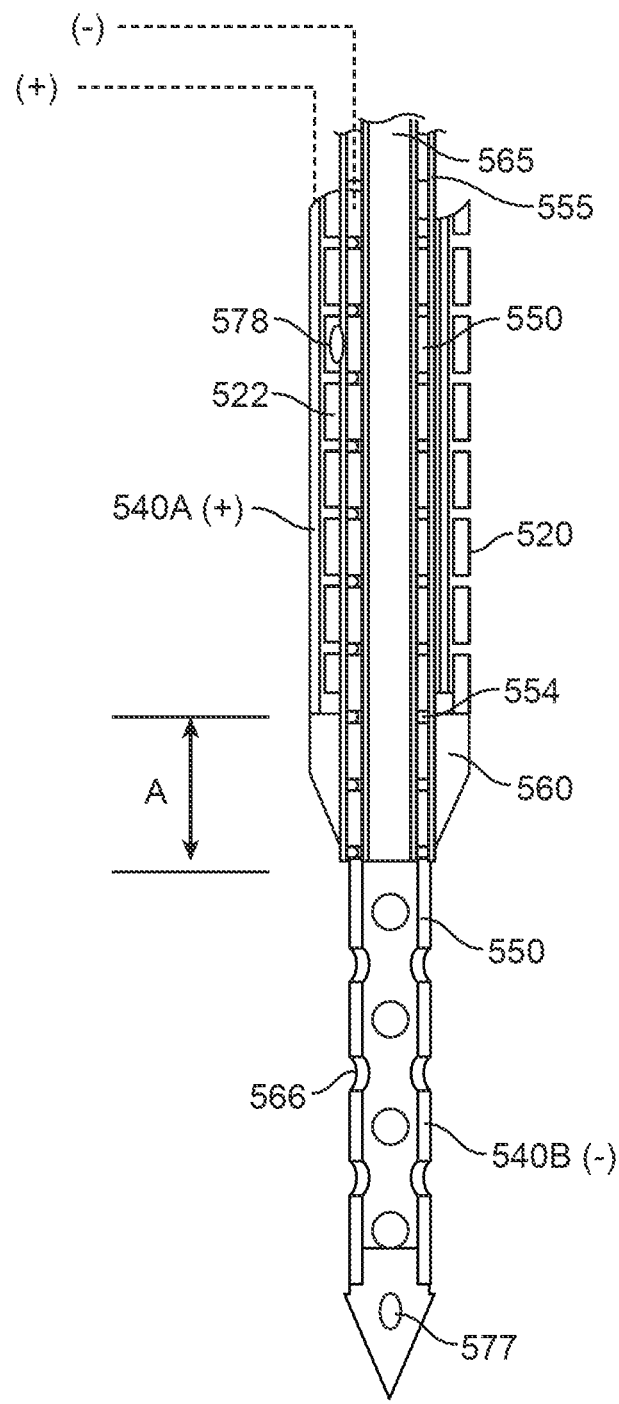
FIG. 19 shows a cross sectional view of the device illustrated in FIG. 18B and also illustrates temperature sensing elements located on device.

FIGS. 17, 18A, 18B and 19, illustrate a variation of the device 500 as having a handle portion 506 coupled to a shaft assembly 510 that extends along axis 512 to the articulating working end 505. The articulating working end 505 can be actuatable as described above. In addition, FIG. 17 shows that handle component 514a can be rotated relative to handle component 514b to cause relative axial movement between a first outer sleeve 520 and second inner sleeve 522 (FIG. 19) to cause the slotted working ends of the sleeve assembly to articulate as described above. The working end 505 of FIG. 19 shows two sleeves 520 and 522 that are actuatable to articulate the working end, but it should be appreciated that a third outer articulating sleeve can be added as depicted above. In one variation, the articulating working end can articulate 90° by rotating handle component 514a between ¼ turn and ¾ turn. The rotating handle component 514a can include detents at various rotational positions to allow for controlled hammering of the working end into bone. For example, the detents can be located at every 45° rotation or can be located at any other rotational increment.

FIG. 17 depict an RF generator 530A and RF controller 530B connectable to an electrical connector 532 in the handle component 514a with a plug connector indicated at 536. The RF generator is of the type known in the art for electrosurgical ablation. The outer sleeve 520 comprises a first polarity electrode indicated at 540A (+). However, any energy modality can be employed with the device.

FIGS. 18A and 18B illustrate yet another variation of a working end of a device for creating cavities in hard tissue. As shown, the device 500 can include a central extendable sleeve 550 with a sharp tip 552 that is axially extendable from passageway 554 of the assembly of first and second sleeves 520 and 522 (FIG. 19). The sleeve 550 can also include a second polarity electrode indicated at 540B (−). Clearly, the first and second electrodes will be electrically insulated from one another. In one variation, and as shown in FIG. 19, the sleeve assembly can carry a thin sleeve 555 or coating of an insulative polymer such as PEEK or Ceramic to electrically isolate the first polarity electrode 540A (+) from the second polarity electrode 540B (−). The electrode can be deployed by rotating knob 558 on the striking surface of handle component 514a (FIG. 17). The degree of extension of central sleeve 550 can optionally be indicated by a slider tab 557 on the handle. In the illustrated variation, the slider tab is located on either side of handle component 514a (FIG. 17). Sleeve 550 can be configured to extend distally beyond the assembly of sleeves 520 and 522 a distance of about 5 to 15 mm.

Referring to FIG. 19, the central extendable sleeve 550 can have a series of slots in at least a distal portion thereof to allow it to bend in cooperation with the assembly of first and second sleeves 520 and 522. In the embodiment shown in FIG. 18B, the central sleeve 550 can optionally include a distal portion that does not contain any slots. However, additional variations include slots on the distal portion of the sleeve.

FIG. 19 further depicts an electrically insulative collar 560 that extends length A to axially space apart the first polarity electrode 540A (+) from the second polarity electrode 540B (−). The axial length A can be from about 0.5 to 10 mm, and usually is from 1 to 5 mm. The collar can be a ceramic or temperature resistant polymer.

FIG. 19 also depicts a polymer sleeve 565 that extends through the lumen in the center of electrode sleeve 550. The polymer sleeve 565 can provide saline infusion or other fluids to the working end and/or be used to aspirate from the working end when in use. The distal portion of sleeve 550 can include one or more ports 566 therein for delivering fluid or aspirating from the site.

Figure 20:
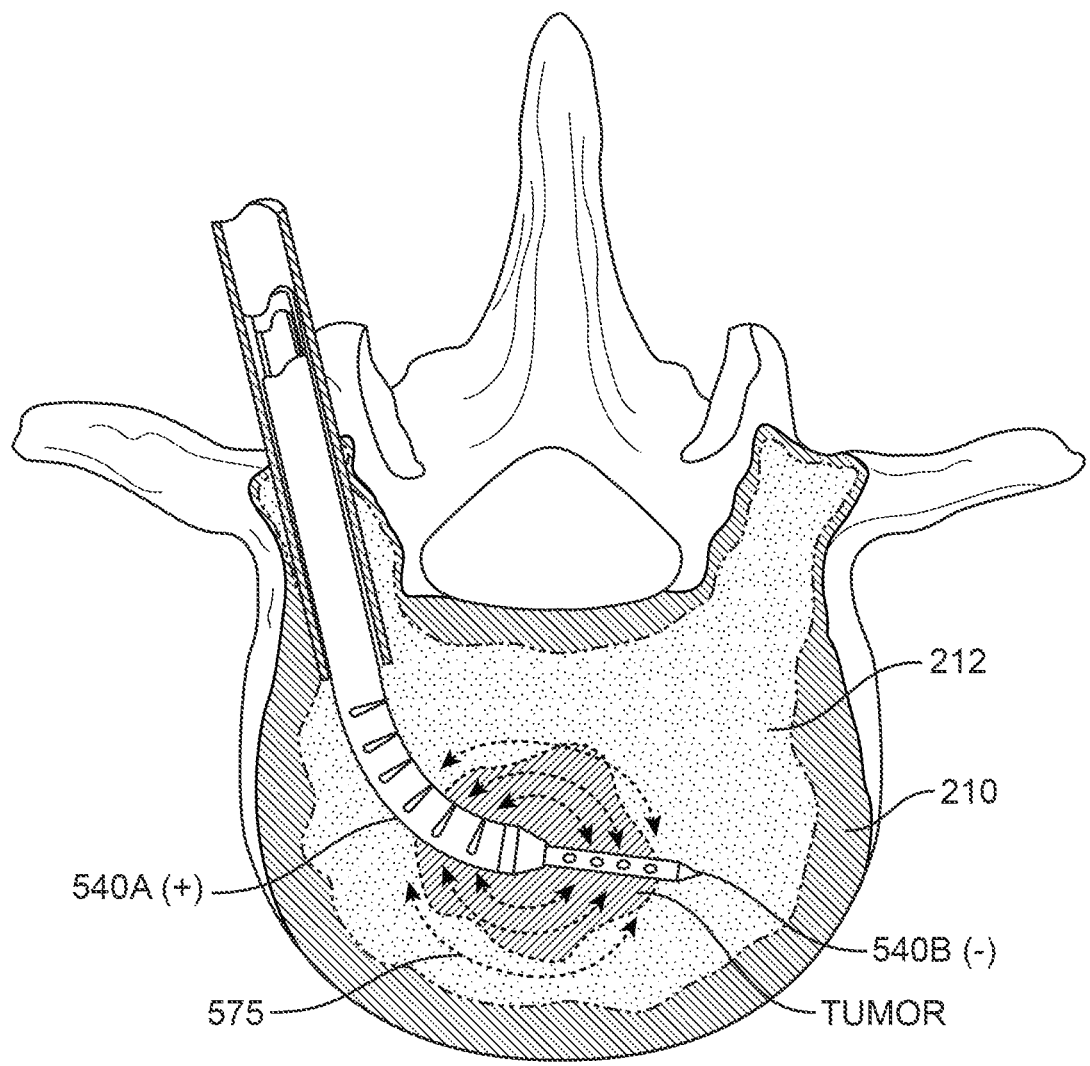
FIG. 20 shows a variation of a device where the inner sleeve is extended from the device and where current is applied between the extended portion of the inner sleeve and the shaft to treat tissue.

In all other respects, the osteotome system 500 can be driven into bone and articulated as described above. The electrodes 540A and 540B are operatively coupled to a radiofrequency generator as is known in the art for applying coagulative or ablative electrosurgical energy to tissue. In FIG. 20, it can be seen that RF current 575 is indicated in paths between electrodes 540A and 540B as shown by lines 575. RF generator 530A and controller 530B for use with the devices described herein can include any number of power settings to control the size of targeted coagulation or ablation area. For example, the RF generator and controller can have Low or power level 1 (5 watts), medium or power level 2 (10 Watts) and High or power level 3 (25 watts) power settings. The controller 530B can have a control algorithm that monitors the temperature of the electrodes and changes the power input in order to maintain a constant temperature. At least one temperature sensing element (e.g., a thermocouple) can be provided on various portions of the device. For example, and as shown in FIG. 19, a temperature sensing element 577 can be provided at the distal tip of sleeve 550 tip while a second temperature sensing element 578 can be provided proximal from the distal tip to provide temperature feedback to the operator to indicate the region of ablated tissue during the application of RF energy. In one example, the second temperature sensing element was located approximately 15 to 20 mm from the distal tip.

Figure 21:
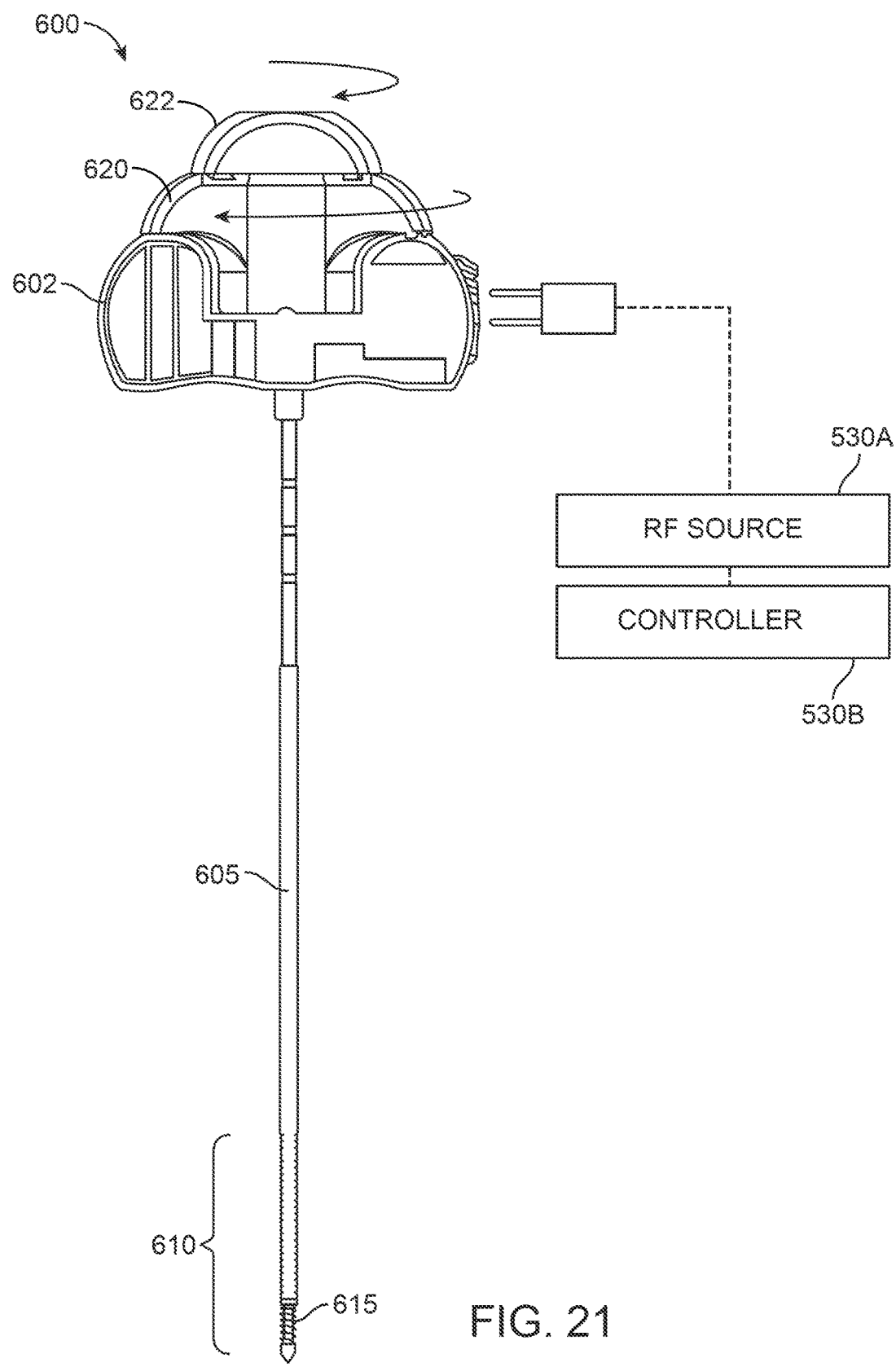
FIG. 21 illustrates a variation of a device as described herein further including an extendable helical electrode carried by the working end of the device.

FIG. 21 illustrates another variation of articulating osteotome 600 with RF ablation features. Variations of the illustrated osteotome 600 can be similar to the osteotome of FIGS. 17-18B. In this variation, the osteotome 600 of has a handle 602 coupled to shaft assembly 610 as described above. The working end 610 again has an extendable assembly indicated at 615 in FIG. 21 that can be extended by rotation of handle portion 622 relative to handle 602. The osteotome can be articulated as described previously by rotating handle portion 620 relative to handle 602.

FIGS. 22A-22B are views of the working end 610 of FIG. 21 in a first non-extended configuration (FIG. 22A) and a second extended configuration (FIG. 22B). As can be seen in FIGS. 22A-22B, the extension portion 615 comprises an axial shaft 624 together with a helical spring element 625 that is axially collapsible and extendible. In one embodiment, the shaft can be a tube member with ports 626 fluidly coupled to a lumen 628 therein. In some variations, the ports can carry a fluid to the working end or can aspirate fluid from the working end.

In FIGS. 22A-22B, it can be seen that axial shaft 624, helical spring element 625 together with sharp tip 630 comprise a first polarity electrode (+) coupled to electrical source 530A and controller 530B as described previously. An insulator 632 separates the helical spring 625 electrode from the more proximal portion of the sleeve which comprises opposing polarity electrode 640 (−). The RF electrodes can function as described above (see FIG. 20) to ablate tissue or otherwise deliver energy to tissue.

In one variation, the extension portion 615 can extend from a collapsed spring length of 2 mm, 3 mm, 4 mm or 5 mm to an extended spring length of 6 mm, 7 mm, 8 mm, 9 mm 10 mm or more. In the working end embodiment 615 in FIG. 22B, the spring can comprise a flat rectangular wire that assists in centering the spring 625 about shaft 624 and still can collapse to short overall length, with the flat surfaces of rectangular wire oriented for stacking. However, other variations are within the scope of the variations described herein.

Of particular importance, it has been found that ability of the osteotome 600 to ablate tissue is greatly enhanced over the embodiment 500 of FIG. 20 by utilizing the helical spring. The use of the spring 625 as an electrode provides significant improvements in delivering energy. This spring provides (i) greatly increased electrode surface area and (ii) a very greatly increased length of relatively sharp edges provided by the rectangular wire—which provides for edges from which RF current can jump. Because the edges provide low surface area the concentration or density of RF current is greater at the edges and allows for the RF current to jump or arc. Both these aspects of the invention—increased electrode surface area and increased electrode edge length—allow for much more rapid tissue ablation.

In one aspect of the invention, the surface area of the spring electrode 625 can be at least 40 mm$^2$, at least 50 mm$^2$, or at least 60 mm$^2$ over the spring electrode lengths described above.

In another aspect of the invention, the total length of the 4 edges of rectangular wire spring can be greater than 50 mm, greater than 100 mm or greater than 150 mm over the spring electrode lengths described above.

In one example used in testing, an osteotome 600 as in FIG. 21-22B was configured with a helical spring that had a collapsed length of 1.8 mm and an extended length of 7.5 mm. In this embodiment, the surface area of the spring electrode 625 when extended was 64.24 mm$^2$ and the total length of the electrodes edges was 171.52 mm (four edges at 42.88 mm per edge).

Figure 22C:
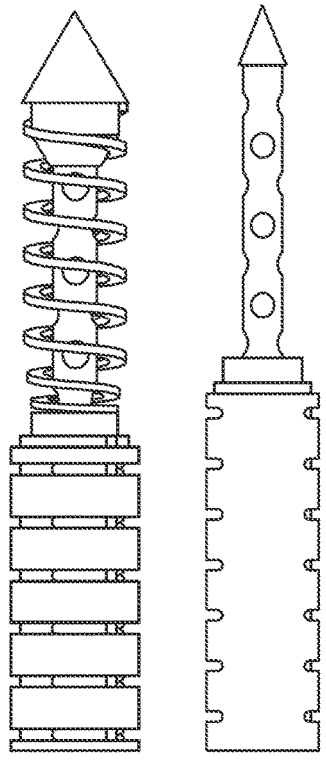
FIGS. 22C and 22D illustrate charts of variations of electrodes having ablated volumes given a particular duration of an ablation cycle.

In a comparison test, a first osteotome without a helical electrode was compared against a second osteotome 600 with a helical electrode as in FIG. 22B. These devices were evaluated at different power levels and different energy delivery intervals to determine volume of ablation. The working ends of the devices had similar dimensions excepting for the helical spring electrode. Referring to FIG. 22C, RF energy was delivered at a low power setting of 5 Watts. It can be seen in FIG. 22C that at a treatment interval of 120 seconds and 5 W, the volume of ablation was about 3 times faster with the helical electrode compared to the working end without the helical electrode (1.29 cc vs. 0.44 cc).

Figure 22D:
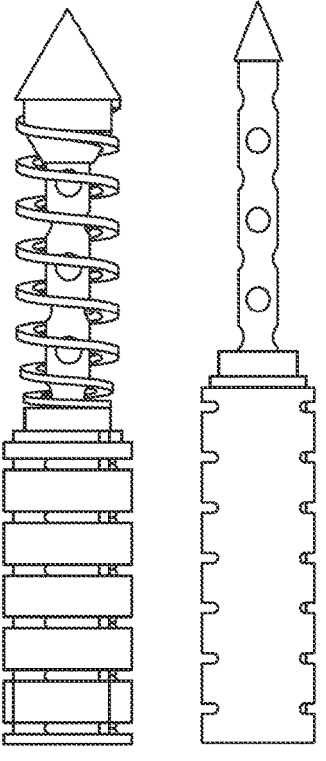

Another comparison test of the same first osteotome 500 (FIG. 18B) and second osteotome 600 with a helical electrode (FIG. 22B) were evaluated at higher 15 Watt power level. As can be seen in FIG. 22D, RF energy at a treatment interval of 25 seconds and 15 W, the volume of ablation was again was about 3 times faster with the helical electrode compared to the working end without the helical electrode (1.00 cc vs. 0.37 cc). Referring to FIG. 22D, the device without the helical electrode impeded out before 60 seconds passed, so that data was not provided. The testing shows that the helical electrode is well suited for any type of tissue or tumor ablation, with a 60 second ablation resulting in 1.63 cc of ablated tissue.

Figure 23:
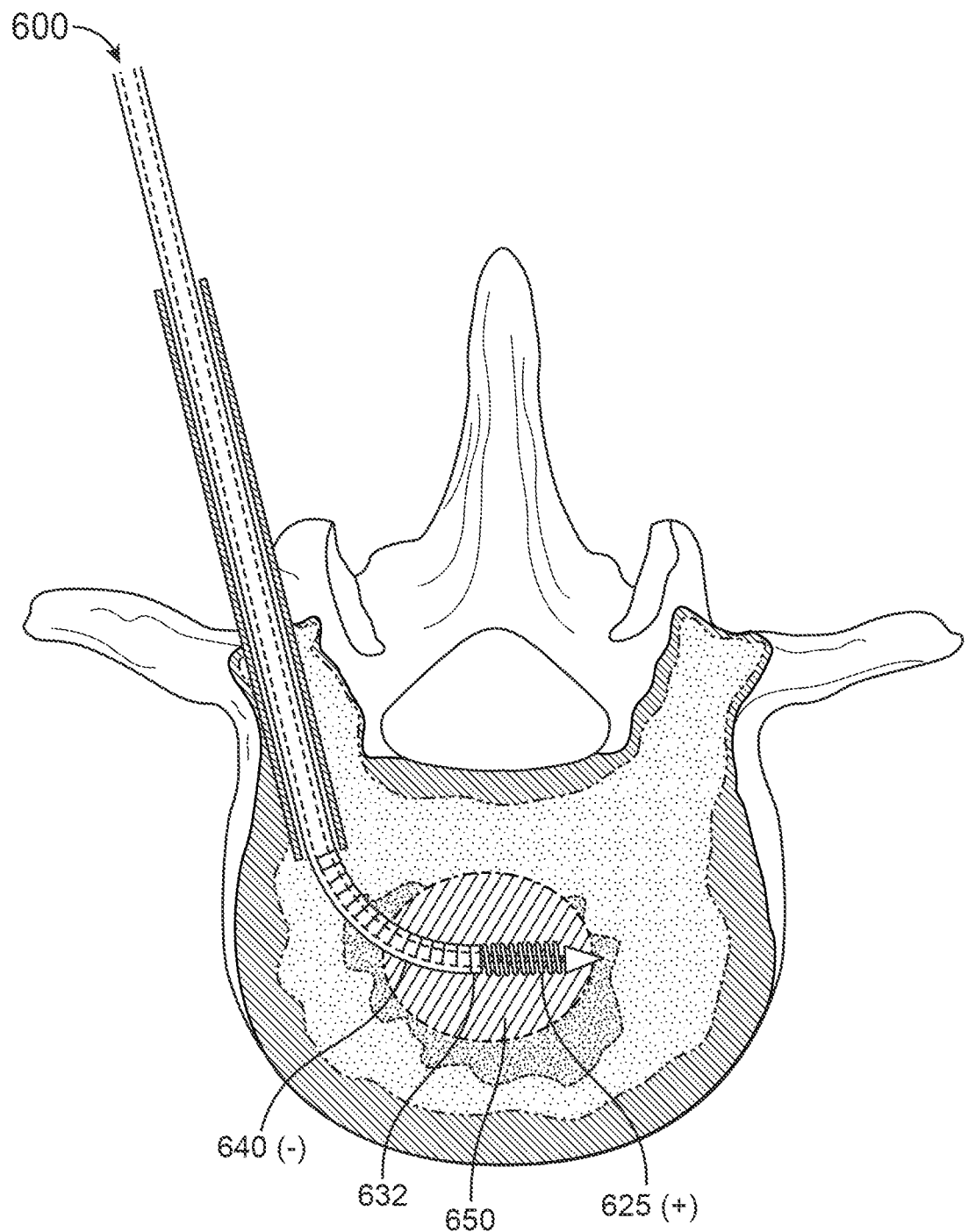
FIG. 23 illustrates the working end of the device of FIG. 21 in a vertebral body with the helical electrode delivering Rf energy to ablate tissue.

FIG. 23 schematically illustrates the osteotome 600 in use in a vertebral body, wherein the RF current between the electrodes 625 and 640 ablate a tissue volume indicated at 640.

Figure 24:
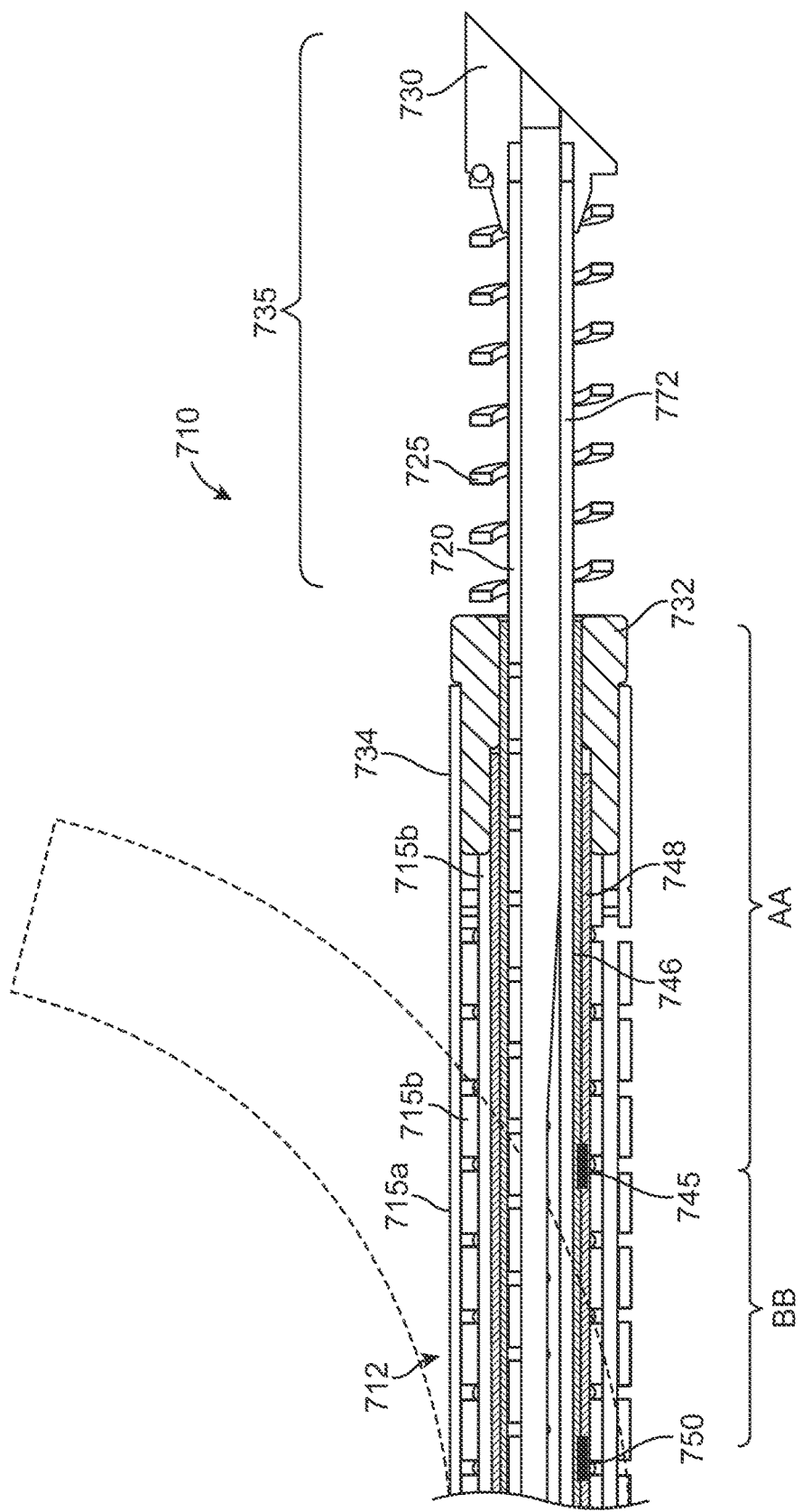
FIG. 24 illustrates the working end of an osteotome similar to that of FIGS. 22A-22B showing temperature sensors disposed within the working end.

FIG. 24 is an enlarged sectional view of a working end 710 of ablation osteotome similar to that of FIGS. 21-22B. In this embodiment, shaft or introducer sleeve assembly 712 has an outside diameter of 4.5 mm or less, or 4.0 mm or less. In one embodiment, the diameter of introducer 712 is 3.5 mm and comprises outer sleeve 715a, intermediate sleeve 715b and inner sleeve 715c all of which are slotted to permit articulation of a portion of the working end as can be seen in phantom view in FIG. 24A.

In FIG. 24, the extendable element or sleeve 720 is shown in an extended configuration which extends helical spring element 725 as described above. In this embodiment, the sleeve 720 and helical spring element 725 together with sharp tip 730 comprises a first polarity electrode coupled to an RF source 530A and controller 530B as described previously. An insulator 732 separates the helical spring 725 electrode from the distal portion 734 of the sleeve which comprises opposing polarity electrode 740. It can be seen that extendable sleeve 720 has a distal portion that is slotted to permit bending as the working end is articulated. The RF electrodes can function as described above (see FIG. 20) to ablate tissue.

In one aspect of the invention, the electrode surface portion of the extendable assembly 735 (sleeve 720 and helical element 725) is moveable from a non-extended position to an extended position during which the electrode surface area varies less than 10% between said non-extended and extended positions. In another embodiment, the electrode surface area varies less than 5% between said non-extended and extended positions. This aspect of the invention allows for similar ablation volumes per unit time no matter the dimension of the extendable assembly 735 since the surface are of the helical element 725 accounts for nearly all of the electrode surface area. The extendable element can have an electrode surface area of at least 40 mm$^2$, at least 50 mm$^2$, or at least 60 mm$^2$.

FIG. 24 further illustrates another aspect of the invention which includes at least one temperature sensor, also referred to as a temperature detecting element, in the working end for controlling or terminating RF energy delivery when tissue adjacent the temperature reaches a predetermined level.

In one variation, as shown in FIG. 24, a temperature detecting element 745 can be disposed between first and second dielectric sleeves 746 and 748 that insulate the introducer sleeve assembly 712 from the extendable sleeve 720. In an embodiment, the RF energy can be activated to ablate tissue until the boundary of ablated tissue adjacent the temperature detecting element 745 reached a predetermined temperature and the temperature detecting element signal can then be coupled to the controller to terminate RF energy delivery. In on embodiment, the temperature detecting element 745 can be disposed between first and second layers of a thin wall dielectric material, 746 and 748, such as PEEK that is used to insulate the opposing polarity electrodes from each other. In FIG. 24, the temperature detecting element 745 can be positioned dimension AA from the distal end of the introducer sleeve assembly 712 which can range from 5 mm to 15 mm FIG. 24 depicts a second temperature detecting element 750 that can be positioned dimension BB from the first temperature detecting element 745 which can be a distance ranging from 5 mm to 15 mm.

As shown FIG. 24, a temperature detecting element 745 can be disposed on an outer radius of an articulated distal portion of the working end. In another embodiment, the temperature detecting element(s) can be disposed on an inner radius of the articulated distal portion of the working end.

Figure 25:
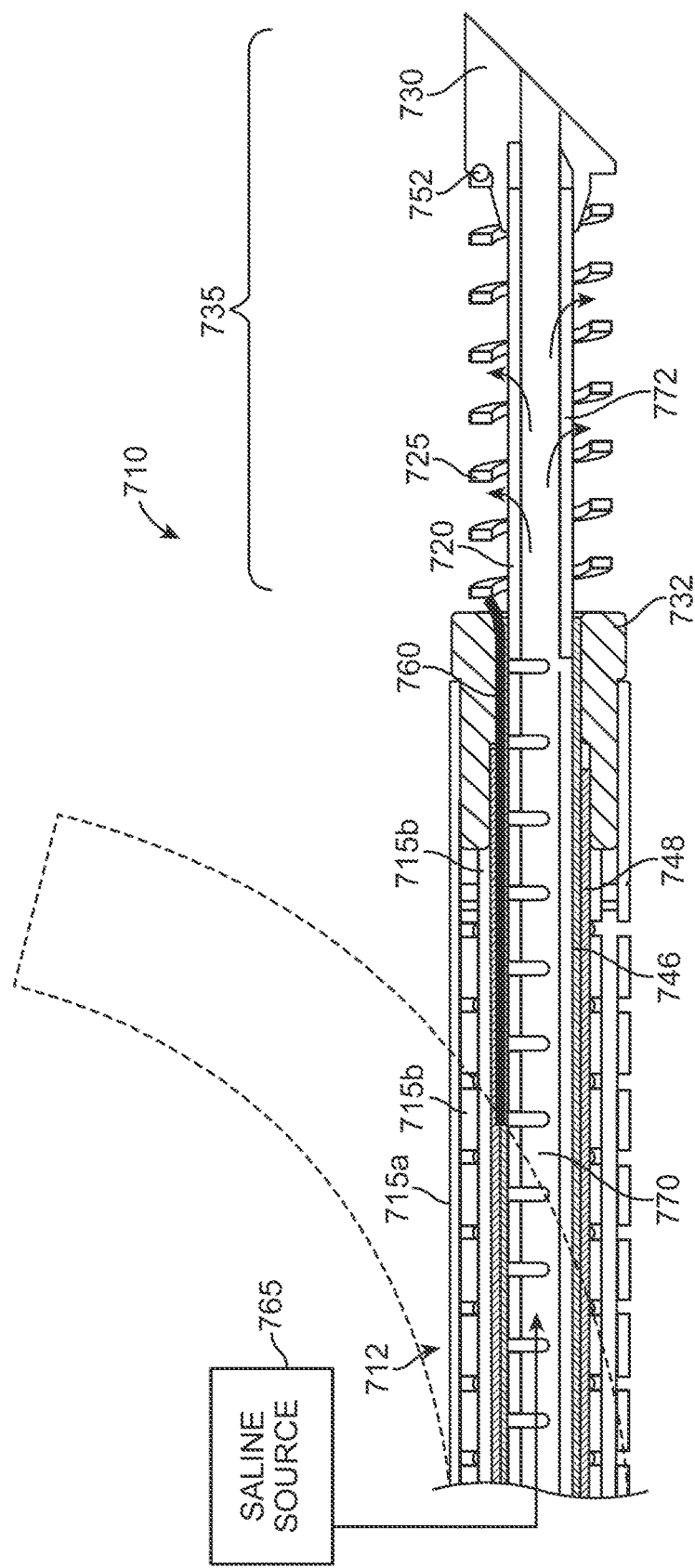
FIG. 25 illustrates another osteotome working end similar to that of FIG. 25.

In FIG. 25, it can be seen that the helical element 725 has a distal end coupled, for example by weld 752, to the distal tip element 730 of the extendable assembly 735. FIG. 25 further shows that helical element 725 has a proximal end coupled to a safety wire 760 that extends proximally and is bonded to the introducer assembly, for example being secured with adhesives or other means between the first and second layers of dielectric material, 746 and 748.

In one embodiment shown in FIG. 25, a conductive fluid source 765 communicates with a lumen 770 extending through the extendable sleeve 720 to provide saline infusion through ports 772 into the region of tissue targeted for treatment.

In general, a method corresponding to the invention comprises introducing an elongated introducer sleeve comprising return electrode into targeted tissue, articulating a distal region of the introducer sleeve and extending an extendable member from the introducer sleeve, wherein the extendable member comprises an active or first polarity electrode having an electrode surface area that varies less than 10% between non-extended and extended positions, and activating an RF source, such that when activated, current flows between the extendable member and the introducer sleeve to apply energy to the targeted tissue. The method includes terminating activation of the RF source when a temperature sensor spaced apart from the first polarity electrode reaches a predetermined temperature. The temperature sensor can be spaced apart from the first polarity electrode by at least 5 mm, 10 mm or 15 mm. The method can target tissue in or near a bone such as a vertebra or long bone. The targeted tissue can be a tumor.

Another method of the invention comprises treating a tumor in or near bone which includes providing an elongated shaft with an articulating working end carrying first and second polarity electrodes, utilizing articulation of the working end to navigate the working end to a position in or near a bone tumor, activating an RF source, such that when activated, current flows between the first and second polarity electrodes to ablate the tumor; and terminating activation of the RF source when a temperature sensor spaced apart from the second polarity electrode reaches a predetermined temperature. In this method, the temperature sensor spacing from an active electrode is configured to provide a predetermined tissue ablation volume. As shown in FIG. 24, the working end can carry a plurality of axially spaced apart temperature sensors, and each sensor can be used to indicate a particular dimension of ablated tissue as each sensor reaches a predetermined temperature based on the expanding volume of ablated tissue.

In another embodiment, the medial and proximal regions of the outer sleeve can be covered with a thin-wall insulative material to provide an distal electrode surface having a predetermined surface area that matches the surface area of the helical element 725. The sleeve 720 at the interior of the helical element also can be covered with a thin-wall dielectric material. In use, the device then would operate in a truly bi-polar manner since the opposing polarity electrodes would have an equal surface area no matter the length of extension of the extendable assembly 735. In general, a device corresponding to the invention would comprise an elongate introducer having a distal end, wherein a surface portion of the introducer comprises an electrode, an extendable member including a helical element comprising an second electrode moveable from a non-extended position to an extended position from the introducer wherein the electrode surface area of the first electrode and the second electrode match no matter the non-extended or extended position of the second electrode.

In another variation of the invention under the present disclosure, the devices, systems and methods described herein can include the use of one or more temperature sensors (also called temperature detecting elements) to monitor, control, and/or otherwise provide a physician with the information needed to ensure a desired treatment.

The temperature sensor/temperature detecting element can comprise any element that can measure temperature of the adjacent tissue or measure temperature of the device immediately adjacent to tissue provide this information to a controller or other portion of the system as described herein. In most variations of the device, the temperature detecting element is used to assess temperature of the tissue before, during, or after application of energy. Examples of temperature detecting elements include thermocouples, resistance temperature detectors (RTDs), optical temperature measurement sensors, pyrometers. In addition, the present disclosure can include any type of temperature measurement device capable of determining a temperature of tissue or even parts of the device that would otherwise indicate a relative temperature of the tissue.

Figure 26A:
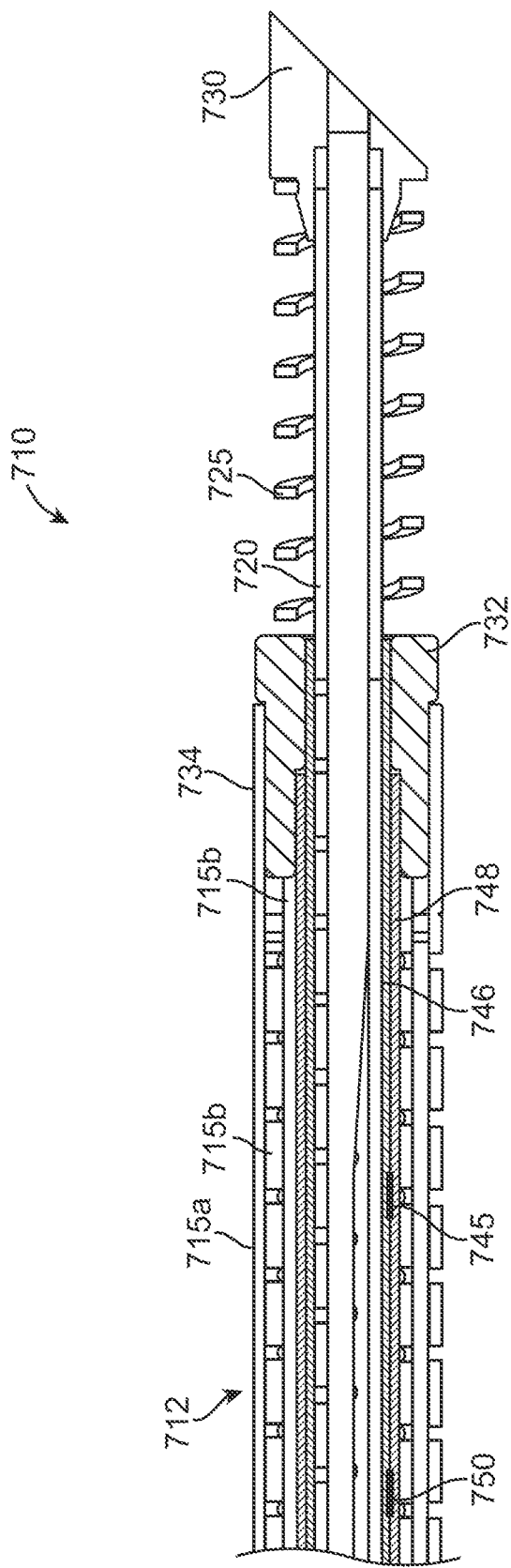
FIGS. 26A to 26E depict variations of devices having multiple temperature sensing elements adjacent to energy transfer portions.

FIG. 26A illustrates a device similar to that shown in FIG. 24 where a temperature detecting element 745 is disposed between first and second dielectric sleeves 746 and 748 that insulate the introducer sleeve assembly 712 from the extendable sleeve 720. As shown the temperature detecting element 745 can be disposed on an outer radius of an articulated distal portion of the working end. In addition, FIG. 26A shows a second temperature detecting element 750 positioned proximally from the first temperature detecting element 745 where spacing of such temperature detecting elements allows for control and/or monitoring a region of heated tissue as described below. However, variations of the devices allow for any number of temperature detecting elements to be used in any number of positions.

Figure 26B:
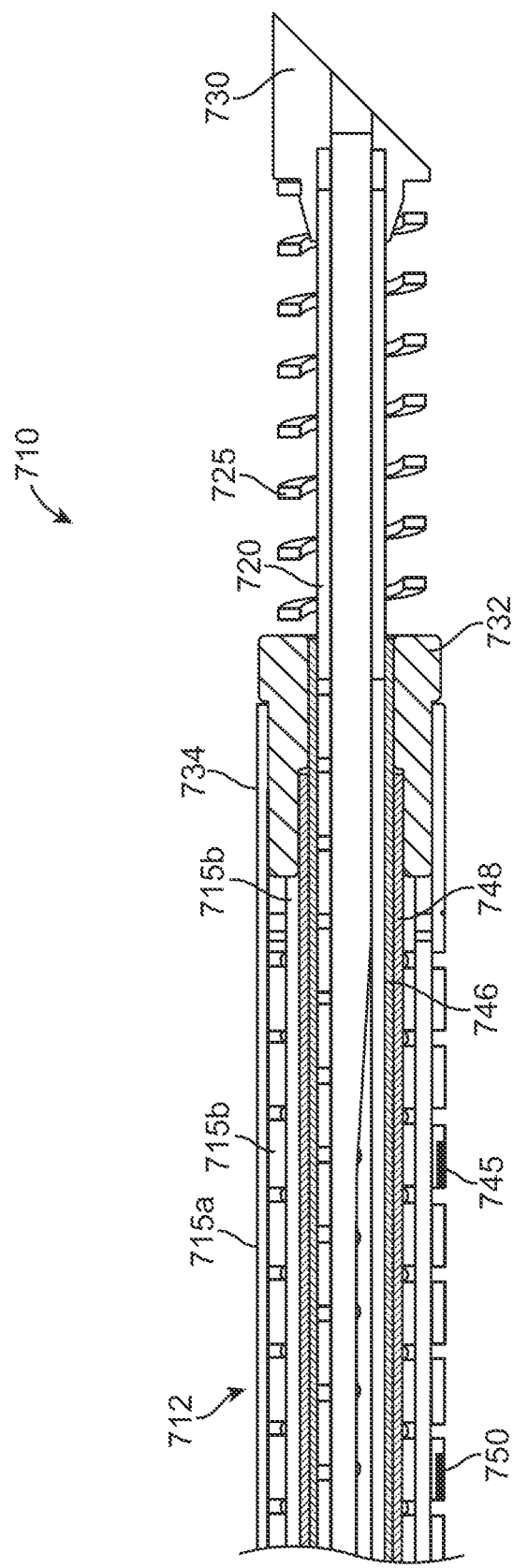

For example, FIG. 26B illustrates two temperature detecting element 245, 250 positioned on an exterior sleeve 715A of the device. In an additional variation, the temperature detecting elements can be positioned in between the slots of the exterior sleeve 715A.

Figure 26C:
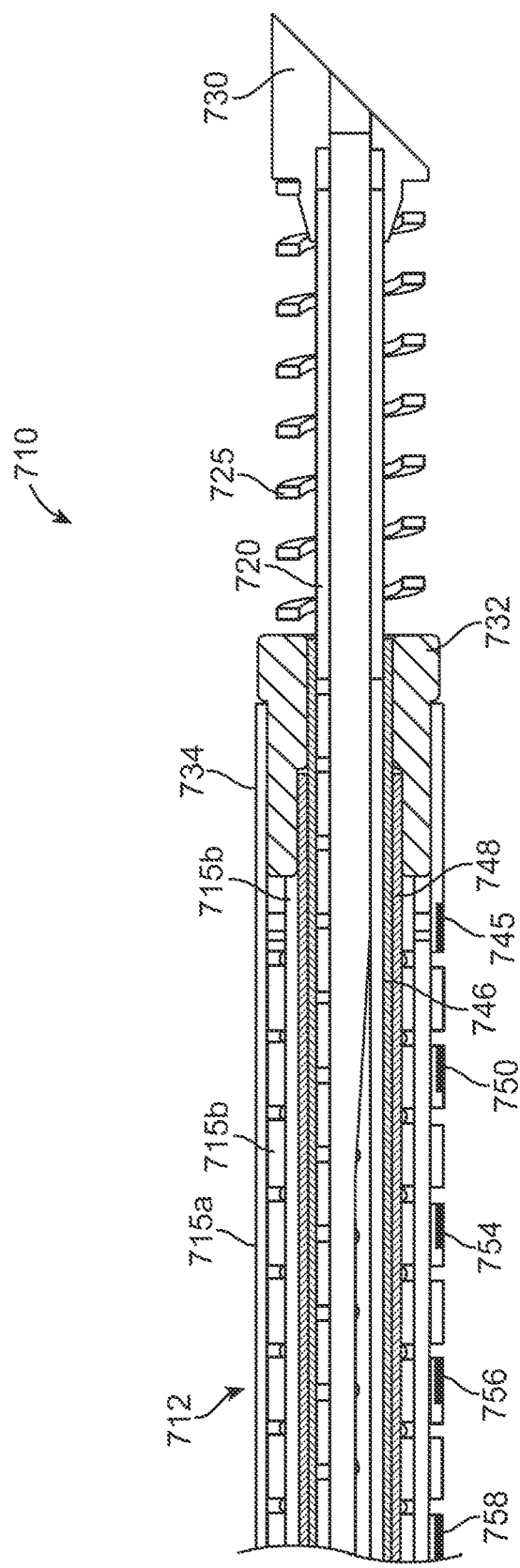
Figure 26D:
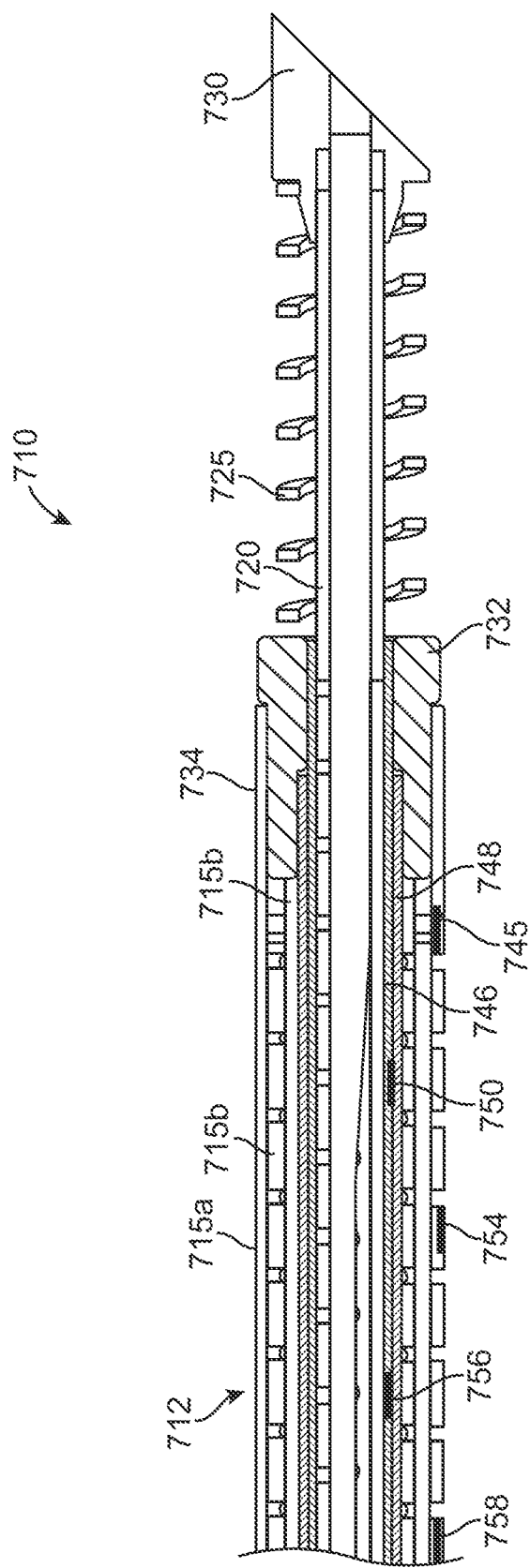
Figure 26E:
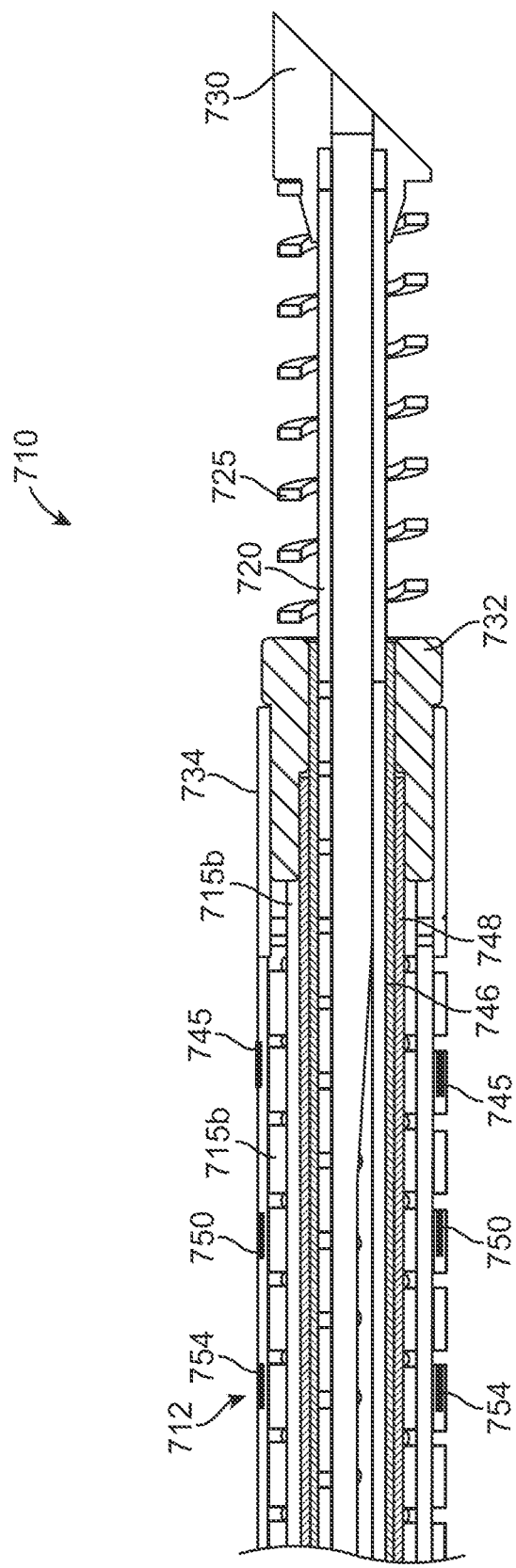

FIG. 26C shows another variation of a device having a plurality of temperature detecting elements 745, 750, 754, 756, 758 spaced along the shaft. Clearly, the temperature detecting elements could be located on an interior of the device, similar to that shown in FIG. 24A. Alternatively, as shown in FIG. 26D, temperature detecting elements can be included both on an interior and exterior of the device. FIG. 26E illustrates temperature detecting elements 745, 750, 754 located on both sides of the device. Alternatively, the temperature detecting element can comprise a ring type element that measures temperature adjacent to a full or partial circumference of the device. As noted herein, the temperature detecting elements can be evenly spaced along the shaft. Alternatively, the spacing of the elements can vary depending upon the intended application of the device. In addition, in most variations of the devices described herein, the temperature detecting elements are located proximally to the heating element of the device. However, additional variations include temperature detecting elements positioned distal to or adjacent to the heating element. The components of the various temperature detecting elements, such as wires, fibers, etc. are not illustrated for purposes of clarity. Furthermore, one or more temperature detecting elements can be positioned on sleeves that move axially relative to the energy transfer portion.

Figure 27A:
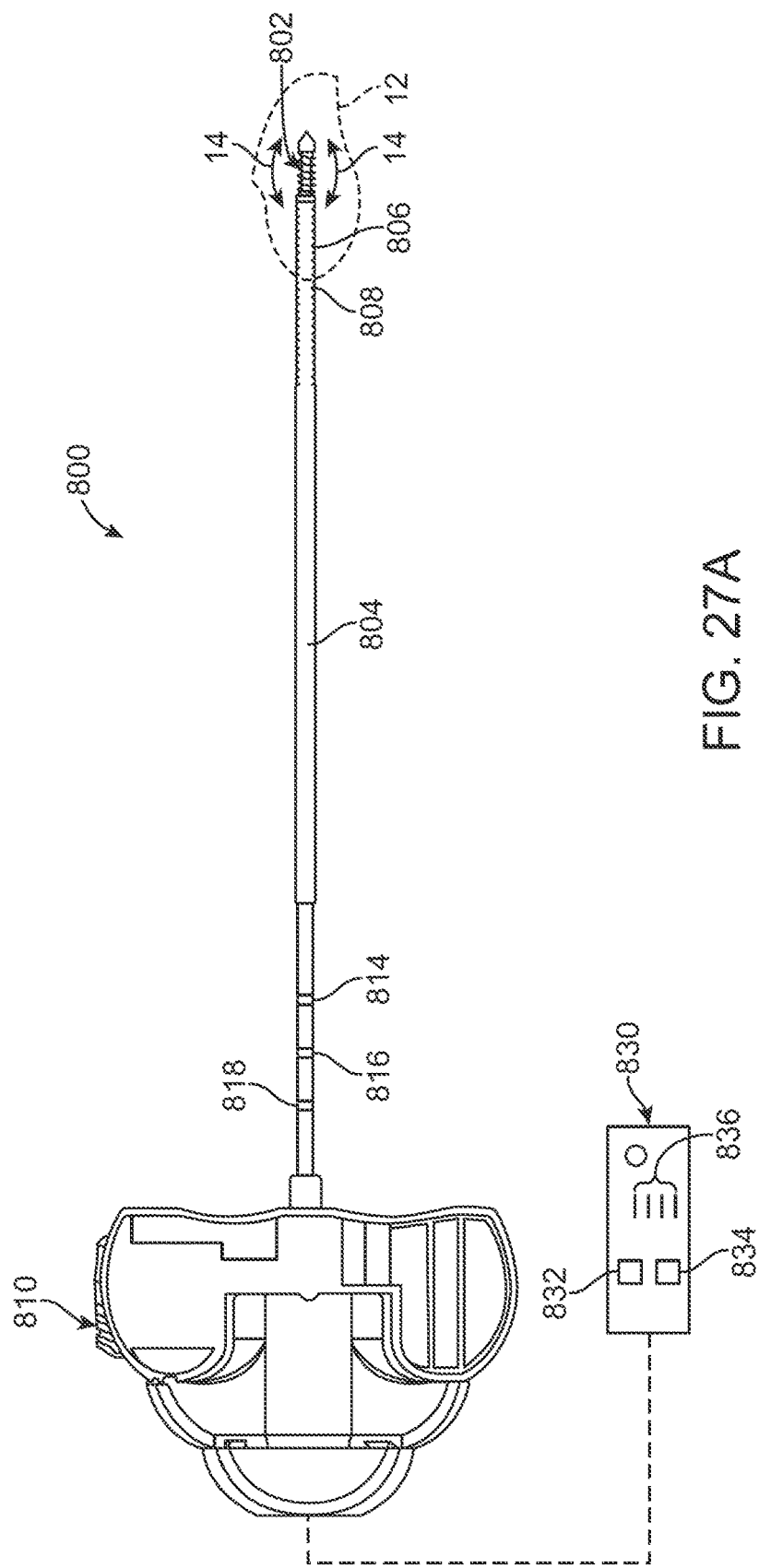
Figure 27B:
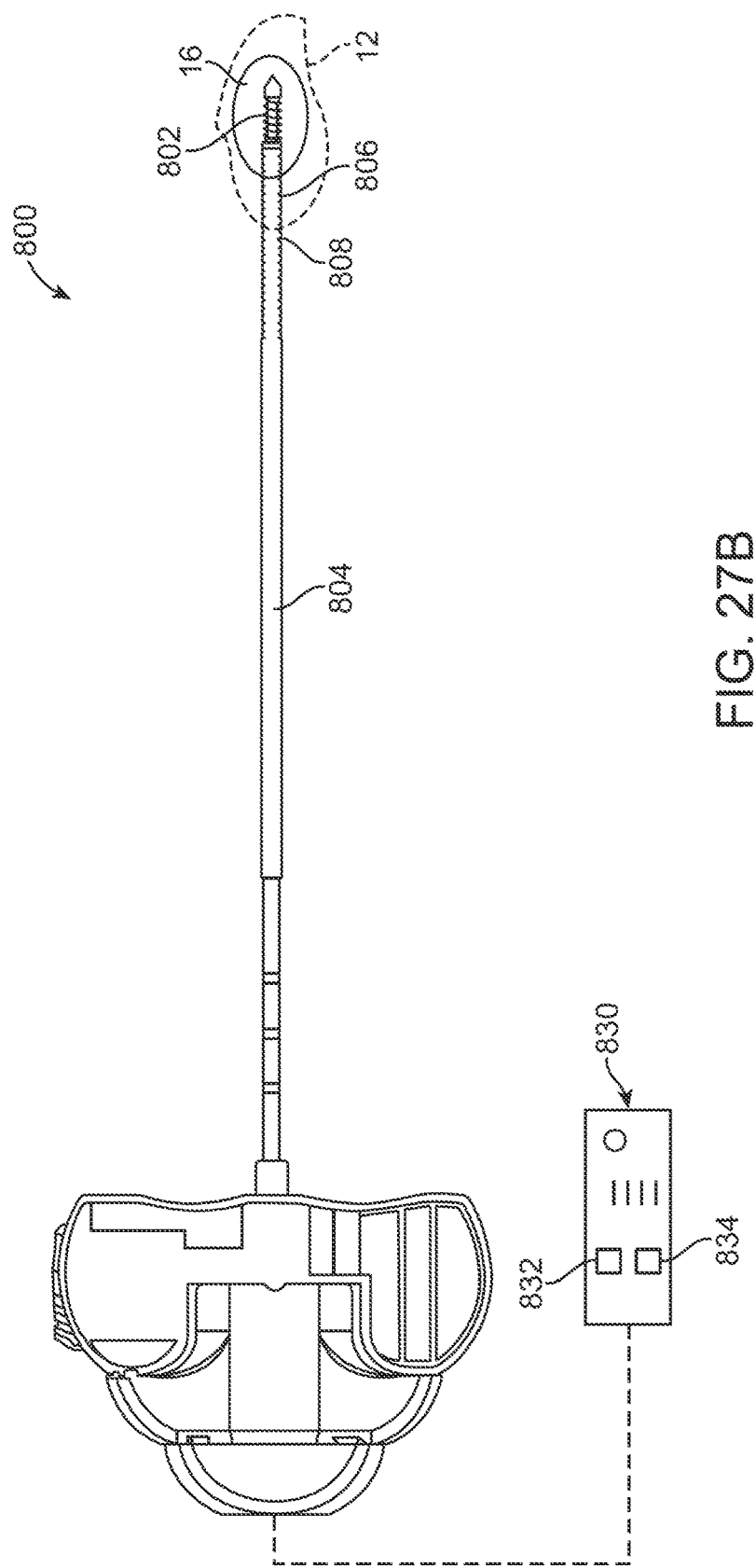

FIGS. 27A to 27C illustrate a concept of using temperature sensing element to guide a treatment where the temperature sensing elements are placed away from the energy transfer unit. FIG. 27A shows an example of a treatment device 800 having energy transfer portion 802 at a distal portion of a shaft 804. As discussed above, one effective variation of a device includes the use of RF energy configuration, either monopolar or bi-polar, that serves as the energy transfer portion. However, any number of energy transfer modes can be employed in the methods, systems and devices described herein where such modalities produced heated tissue. Such modalities can include, but are not limited to, resistive heating, radiant heating, coherent light, microwave, and chemical. In yet another variation, the devices can use radioactive energy modalities as well. Alternatively, variations of devices employing temperature based detection can employ cryosurgical energy configurations that rely upon the application of extreme cold treat tissue. Clearly, in such cases the methods, devices, and systems would monitor regions of cooled tissue rather than heated tissue.

Turning back to FIG. 27A, the treatment device 800 includes at least a first temperature detecting element 806 located axially relative to an energy transfer element 802. In some variations, the energy transfer element 806 is located proximally along an axis of the shaft from thee energy transfer unit 802. However, as described above, variations of the devices include placement of the temperature detecting elements as needed. FIG. 27A also shows a second temperature detecting element 808 located proximally to the first temperature detecting element 806. Again, the methods and procedures described herein can employ any number of temperature detecting elements.

The devices and methods also optionally include conveying temperature information on a controller 830. Variations of the controller 830 allow for display or conveyance of temperature information specific to each temperature detecting element. For example, in the variation shown in FIG. 27A, the first temperature detecting element can be coupled to display 832 while the second temperature detecting element 808 can be coupled to display 834. The controller can also optionally allow a physician to set temperature limits based on readings from each temperature sensing element. In such a case, if a measured temperature at a respective temperature sensing element exceeds the temperature limit, the system can end delivery of the energy or provide any other auditory or visual alert. The control unit 830 can be separate from a power supply or can be integrated into the power supply. Additional variations also include a control unit that can be integrated into a handle or other portion of the device 800.

In a first variation, a physician can position the distal end of the shaft 804 containing the energy transfer element 802 within a tumor 12. Clearly, the methods and procedures are not limited to treatment of a tumor. Instead, the device can be positioned in any target region that a physician seeks to treat. Once the device 800 and energy transfer element 802 are properly positioned, the physician can begin to apply energy to the energy transfer portion to cause an effect (as shown by arrows 14) in tissue that produces a region of affected tissue, e.g., a temperature of the tissue increases or decreases (as described above based on the energy modality used). For convenience, the method shall be discussed with respect to an area of heated tissue. Clearly, alternate variations of the device involve regions of cooled tissue.

FIG. 27B illustrates continued application of energy, which results in expansion of the region of heated tissue 16. The continued application of energy can occur intermittently or continuously. As the physician operates the device 800, the temperature detecting elements 806, 808 can monitor temperature of adjacent tissue. FIG. 27B depicts the region of heated tissue 16 as not having yet reached the first or second temperature sensing element 806, 808. The temperature measurements can occur intermittently, continuously, during application of energy, or in between intermittent applications of energy. Likewise, the temperature information 832, 834 can optionally be relayed to the controller 830.

FIG. 27C shows the heated region of tissue 16 expanded sufficiently such that it encompasses the desired region of tissue 12 or tumor. FIG. 27 also depicts the heated region of tissue 16 as being easily visually identified. However, during an actual treatment, the physician simply cannot observe the actual perimeter of the zone of heated tissue 16. Instead, the temperature detecting elements 806, 808 will be able to detect the heated region of tissue 16 as the temperature of the tissue adjacent to the temperature detecting elements 806, 808 rises.

The temperature measured by the temperature detecting elements 806, 808 can also provide the physician with the ability to monitor the progression of the region of heated tissue 16. For instance, the volume, length, area, or other characteristic of the region of heated tissue can be approximated by obtaining a temperature that is associated with the perimeter of the region. Analytic correlation of this associated temperature to the physical characteristic of the heated tissue can be determined from bench testing, animal testing, cadaver testing, and/or computer analysis. Such analytic correlation allows the volume of an area of heated tissue to be approximated based on the temperature of the outer perimeter of that region. In the illustrated example of FIG. 27C, there exists a pre-determined temperature associated with an area of heated tissue having known dimension. Once the measured temperature at temperature detecting element 808 reaches this associated temperature, the physician can stop the treatment. Alternatively, or in addition, the system or controller 830 can include safety algorithms to automatically warn the physician to cease treatment or even to perform a safety shutoff of the system if a given temperature is reached or if the temperature remains constant while power is applied to the electrode.

In additional variations, the monitoring of the size or profile of the region of heated tissue can be used to control the application of applied energy. For example, as the measured temperature approaches the associated temperature, the controller can reduce power to prevent any lags in measurement from overshooting the target treatment zone.

The variation described above in FIGS. 27A to 27C can also be used to position the device 800 relative to a desired target region 12. For example, the temperature detecting elements 806, 808, can be radiopaque (or can have radiopaque markers) so that a physician can place the appropriate temperature detecting element in a target area or at a perimeter of the target area. In the example shown in FIG. 27A, a physician could position the second temperature detecting element 808 just outside of a tumor or as otherwise desired. Once the measured temperature reaches the associated temperature the physician can stop application of energy and reposition the device as needed or stop treatment.

E.g. A physician may choose to use 50 C or 55 C as a target temperature for a specific temperature detecting element based on pre-planning. Once that temperature reaches the desired level; e.g. 50 C or 55 C then the physician may stop delivering any further energy to the tissue by turning off energy delivery. In another embodiment, controller will have an algorithm where a physician inputs the desired temperature for a specific temperature detecting element and controller will apply energy. Energy delivery will stop once the desired temperature is achieved. Further enhancement to the controller may also allow physician with an ability to set desired amount of time associated with each target temperature where controller will maintain energy level sufficient to control the temperature for desired amount of time and then turn off the energy delivery.

FIG. 27A also depicts a variation of the device as having visible markers 814, 816, and 818 located on a shaft. The markers can be used to assist the physician in positioning of the energy transfer elements and/or temperature detecting elements. For example, in the illustrated variation, the device can be used with an introducer cannula of a known size so that marker 814 informs the physician that the distal tip or energy transfer element is positioned at the opening of the cannula. Likewise, markers 816 and 818 can inform the physician that energy transfer elements 806 and 808 are respectively located at the opening of the cannula.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

We claim:

1. A medical device for creating regions of heated tissue using temperature to monitor a desired profile of the regions, the medical device, comprising:
    a shaft coupled to a handle, where the handle includes a connector for electrically coupling to an energy controller;
    a first temperature detecting element spaced axially and proximally along the shaft from a distal end of a bi-polar energy transfer portion;
    a second temperature detecting element spaced axially and proximally along the shaft from a proximal end of the bi-polar energy transfer portion; where the first and second temperature detecting elements are configured to independently and respectively provide a first and a second actual temperature measurement; and
    where the energy controller is configured to deliver energy to the bi-polar energy transfer portion, control delivery of the energy, and to compare at least one of the first or second actual temperature measurements to at least one associated temperature correlating to a previously measured region of heated tissue having a known profile to produce the regions of heated tissue having the desired profile;
    further comprising an introducer cannula having a length, where the shaft further includes a first and a second visual marker on a proximal end of the shaft adjacent to the handle, where each of the first and the second visual markers corresponds to a respective one of the first or second temperature detecting element, such that when placed within the introducer cannula, the first and the second visual markers allow determination of whether the respective one of the first or second temperature detecting element is distally adjacent to an end of the introducer cannula; and
    wherein the medical device is configured to create the heated tissue.

2. The medical device of claim 1, where the shaft includes an articulating portion where the bi-polar energy transfer portion is located distally to the articulating portion.

3. The medical device of claim 1, the shaft and the handle are configured to receive an impact force applied on the handle and transfer the impact force to a distal end of the shaft.

4. The medical device of claim 1, where the energy controller comprises an extendable element and a portion of the shaft, where the extendable element is configured to extend axially relative to a distal end of the shaft.

5. The medical device of claim 1, where at least one of the first or second temperature detecting elements is axially moveable along the shaft independently of the bi-polar energy transfer portion.

6. A medical system for creating regions of heated tissue from tissue using temperature to monitor a desired profile of the regions of heated tissue, the medical system comprising:
    an energy controller capable of controlling energy delivery in response to comparing at least one temperature measurement to at least one associated temperature, where the at least one associated temperature correlates to a previously measured region of heated tissue having a known profile;
    a treatment device having a shaft coupled to a handle, where the handle includes a connector for electrically coupling to the energy controller; and
    a shaft extending from the handle to a distal portion, an energy transfer portion for delivering the energy from a power supply to the tissue located at the distal portion;
    at least a first and second temperature detecting element spaced proximally from a proximal end of the energy transfer portion, each temperature sensor of the first and second temperature detecting elements configured to independently and respectively provide a first and a second actual temperature measurement to the energy controller; and
    wherein the medical system is configured to deliver the energy to the tissue to create the regions of heated tissue using temperature to monitor the desired profile of the regions of heated tissue.

7. The medical system of claim 6, where the shaft includes an articulating portion.

8. The medical system of claim 6, the shaft and the handle are configured to receive an impact force applied on the handle and transfer the impact force to a distal end of the shaft.

9. The medical system of claim 6, where the energy controller comprises an extendable element and a portion of the shaft, where the extendable element is configured to extend axially relative to a distal end of the shaft.

10. The medical system of claim 6, where at least one of the first or second temperature detecting elements is axially moveable along the shaft independently of the energy controller.

11. The medical system of claim 6, further comprising an introducer cannula having a length, where the shaft further includes a first and a second visual marker on a proximal end of the shaft adjacent to the handle, where each of the first and second visual markers correspond to a respective one of the at least first and second temperature detecting elements, such that when placed within the introducer cannula, the first and second visual markers allow determination of whether the respective one of the at least first or second temperature detecting elements is distally adjacent to an end of the introducer cannula.

\* \* \* \* \*

UNITED STATES PATENT AND TRADEMARK OFFICE
CERTIFICATE OF CORRECTION

PATENT NO. : 10,028,784 B2
APPLICATION NO. : 14/453427
DATED : July 24, 2018
INVENTOR(S) : Steve Kramer et al.

It is certified that error appears in the above-identified patent and that said Letters Patent is hereby corrected as shown below:

Column 20, Line 30 In Claim 6 reads, ". . . transfer portion, each temperature sensor of the first and . . ." which should read, ". . . transfer portion, each of the first and . . ."

Signed and Sealed this
Twenty-second Day of January, 2019

Andrei Iancu
*Director of the United States Patent and Trademark Office*